United States Patent
Ford et al.

(10) Patent No.: US 10,983,137 B2
(45) Date of Patent: Apr. 20, 2021

(54) DIAGNOSIS OF LEUKOCYTE-MEDIATED DISEASE AND HALOGEN GAS EXPOSURE

(71) Applicant: Saint Louis University, St. Louis, MO (US)

(72) Inventors: David A. Ford, St. Louis, MO (US); Mark A. Duerr, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 641 days.

(21) Appl. No.: 15/545,307

(22) PCT Filed: Jan. 19, 2016

(86) PCT No.: PCT/US2016/013834
§ 371 (c)(1),
(2) Date: Jul. 20, 2017

(87) PCT Pub. No.: WO2016/118468
PCT Pub. Date: Jul. 28, 2016

(65) Prior Publication Data
US 2018/0003726 A1  Jan. 4, 2018

Related U.S. Application Data

(60) Provisional application No. 62/106,049, filed on Jan. 21, 2015.

(51) Int. Cl.
*G01N 33/92* (2006.01)
*G01N 33/68* (2006.01)

(52) U.S. Cl.
CPC ......... *G01N 33/92* (2013.01); *G01N 33/6893* (2013.01); *G01N 2800/102* (2013.01); *G01N 2800/26* (2013.01); *G01N 2800/42* (2013.01)

(58) Field of Classification Search
CPC .............. G01N 33/92; G01N 33/6893; G01N 2800/102; G01N 2800/26; G01N 2800/42
See application file for complete search history.

(56) References Cited

U.S. PATENT DOCUMENTS

2011/0091980 A1   4/2011   Ford
2012/0035074 A1   2/2012   Witztum et al.

OTHER PUBLICATIONS

Albert et al., "Eosinophil Peroxidase-derived Reactive Brominating Species Target the Vinyl Ether Bond of Plasmalogens Generating a Novel Chemoattractant, α-Bromo Fatty Aldehyde," *J. Biol. Chem.*, 278:8942-8950, 2003.
Cooper and Hanigan, "Enzymes involved in processing glutathione conjugates," In *Comprehensive Toxicology* (McQueen, C. A. ed.), 2nd Ed., Elsevier. pp. 323-365, 2010.
Duerr et al., "Identification of glutathione adducts of α-chloro fatty aldehydes produced in activated neutrophils," *J. Lipid Res.*, 56(5):1014-1024, 2015.
Ford, "Lipid oxidation by hypochlorus acid: chlorinated lipids in atherosclerosis and myocardial ischemia," *Clin. Lipidol.* 5(6):838-852, 2010.
International Preliminary Report on Patentability issued in corresponding PCT Application No. PCT/US2016/013834, dated Jul. 25, 2017.
International Search Report and Written Opinion issued in corresponding PCT Application No. PCT/US2016/013834, dated Mar. 30, 2016.
Thukkani et al., "Myeloperoxidase-derived Reactive Chlorinating Species from Human Monocytes Target Plasmalogens in Low Density Lipoprotein," *J. Biol. Chem.*, 278:36365-36372, 2003.
Thukkani et al., "Neutrophil-mediated accumulation of 2-ClHDA during myocardial infarction: 2-ClHDA-mediated myocardial injury," *Am. J. Physiol. Heart Circ. Physiol.*, 288:H2955-2964, 2005.
Ullen et al., "Mouse brain plasmalogens are targets for hypochlorous acid mediated modification in Vitro and in Vivo," *Free Rad. Biol. Med.*, 49(11):1655-1665, 2010.
Wildsmith et al., "Metabolism of Myeloperoxidase-derived 2-Chlorohexadecanal," *J. Biochem.*, 281(25):16849-16860, 2006.

*Primary Examiner* — Christopher Adam Hixson
(74) *Attorney, Agent, or Firm* — Parker Highlander PLLC

(57) ABSTRACT

Described are glutathione adducts of fatty aldehydes (FALD-GSH) and methods useful in the detection of FALD-GSH in the identification of pathologies associated with leukocyte-mediated disease conditions, including eosinophil and neutrophil activation. Thus, the present disclosure provides methods of diagnosing a subject as having or being at risk of developing a leukocyte-mediated disease (LMD) comprising (a) detecting the level of glutathione adducts of 2-halofatty aldehydes (FALD-GSH) in a sample; (b) comparing the amount of FALD-GSH with a control or standard reflective of diseased and/or healthy levels of FALD-GSH; and (c) diagnosing the subject as having or being at risk of developing LMD if the level of FALD-GSH in the sample is higher than the control or standard.

15 Claims, 14 Drawing Sheets

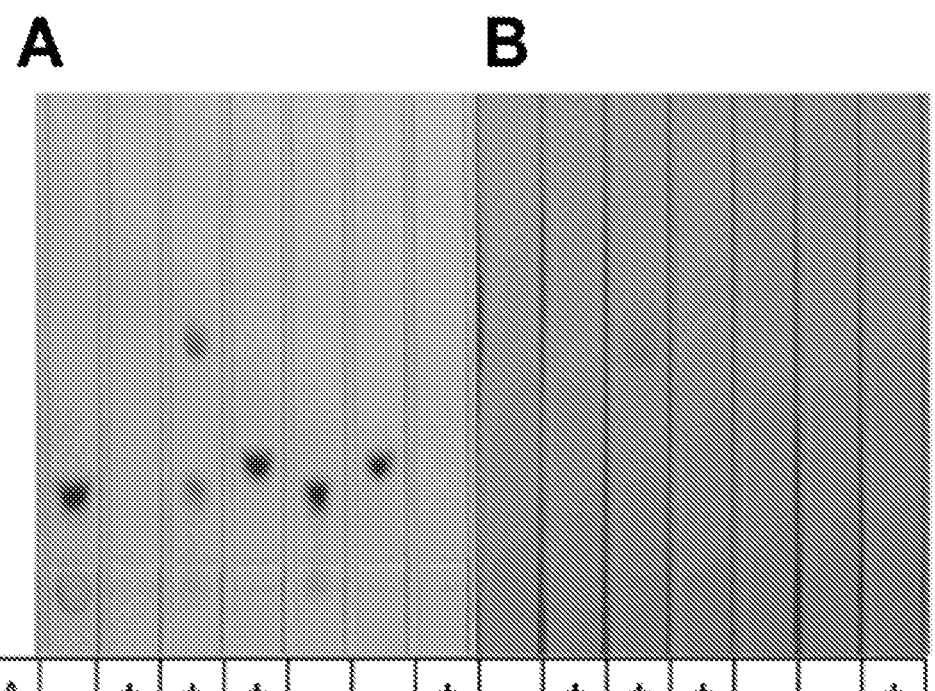
FIGS. 1A-B

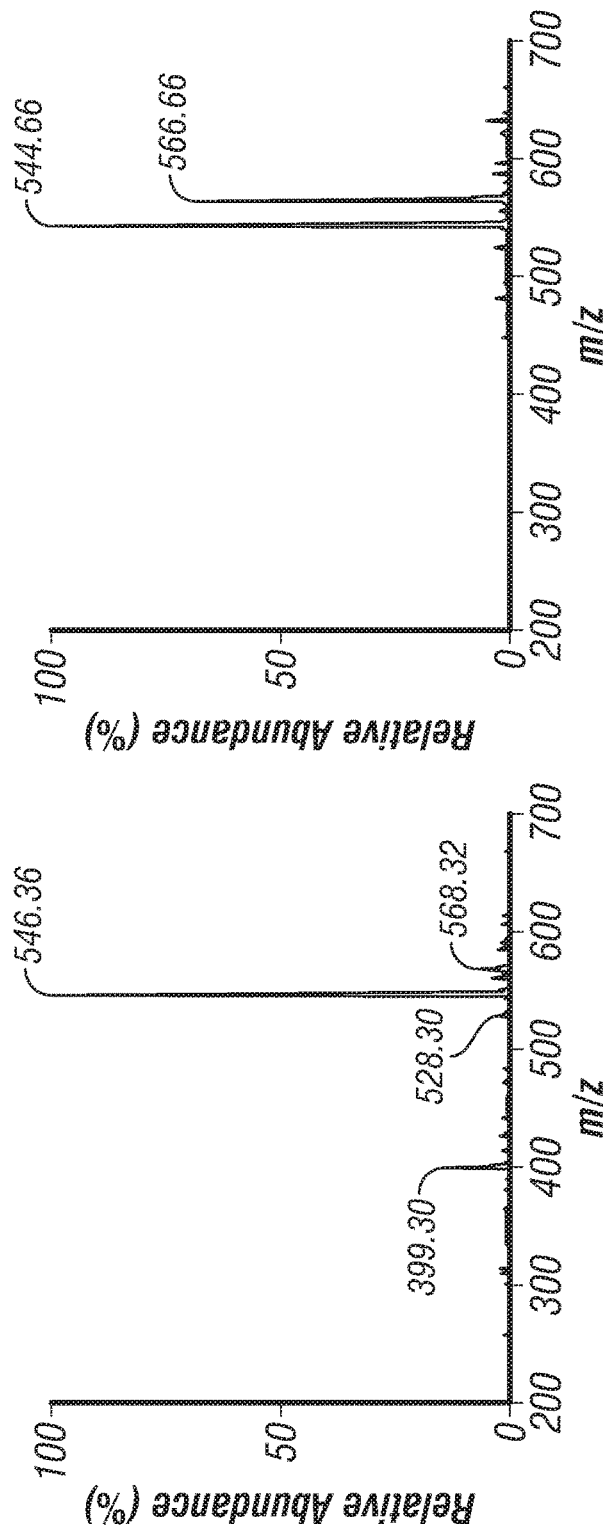
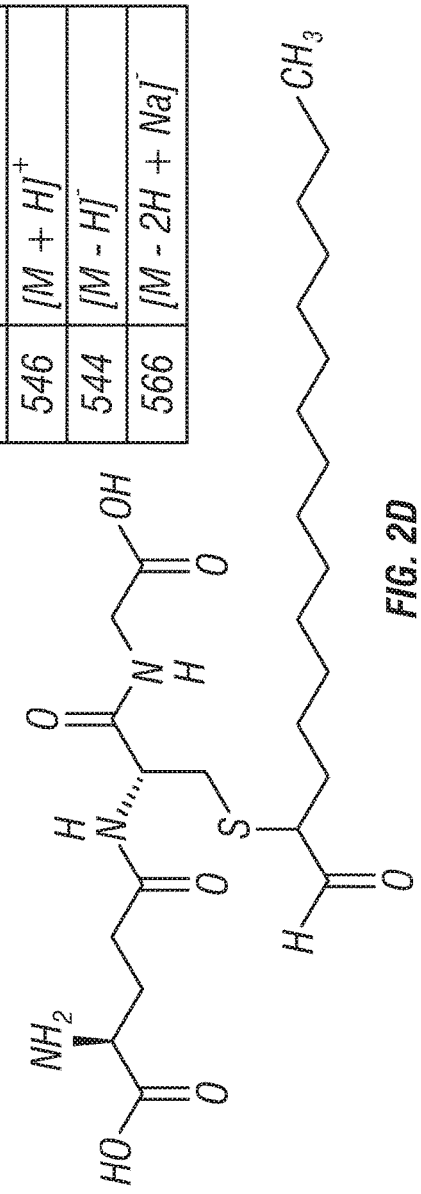
FIG. 2A
FIG. 2B
FIG. 2C
FIG. 2D

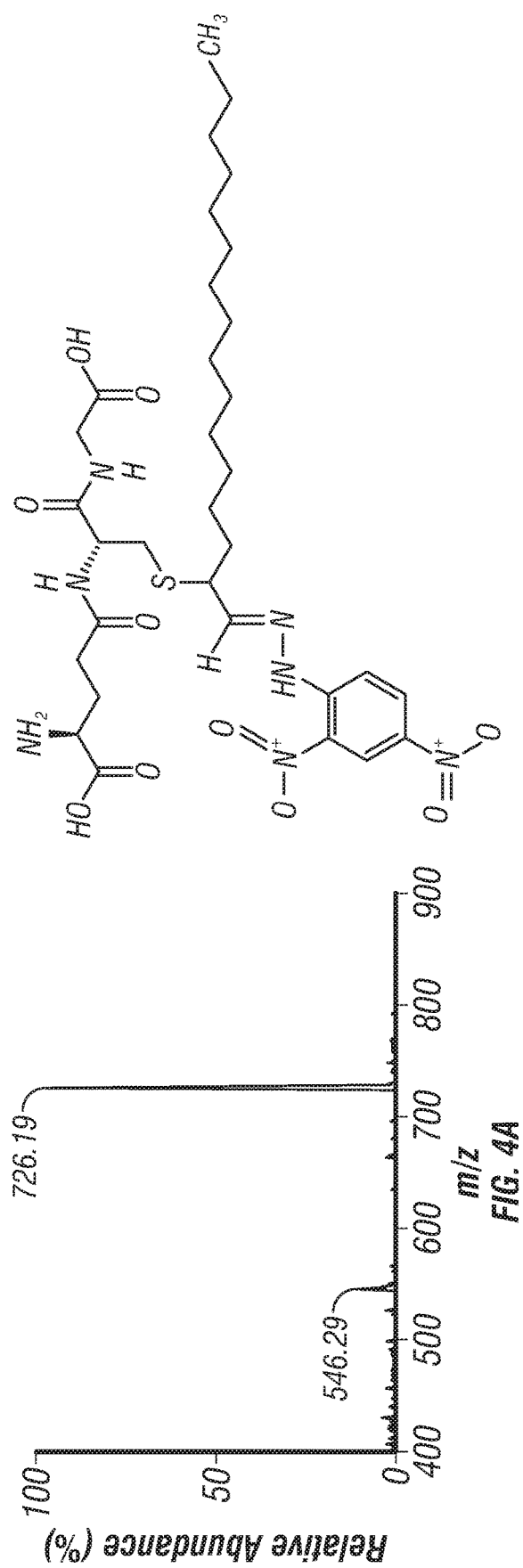
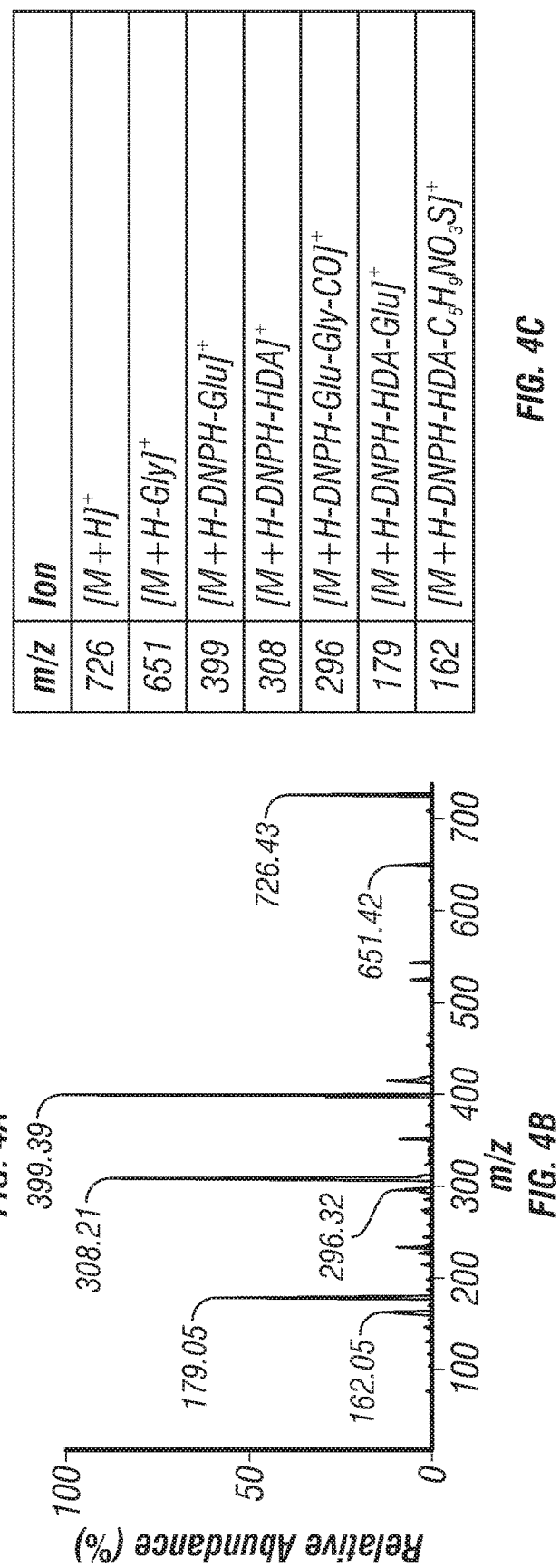
FIG. 4A
FIG. 4B
FIG. 4C

FIGS. 6A-B

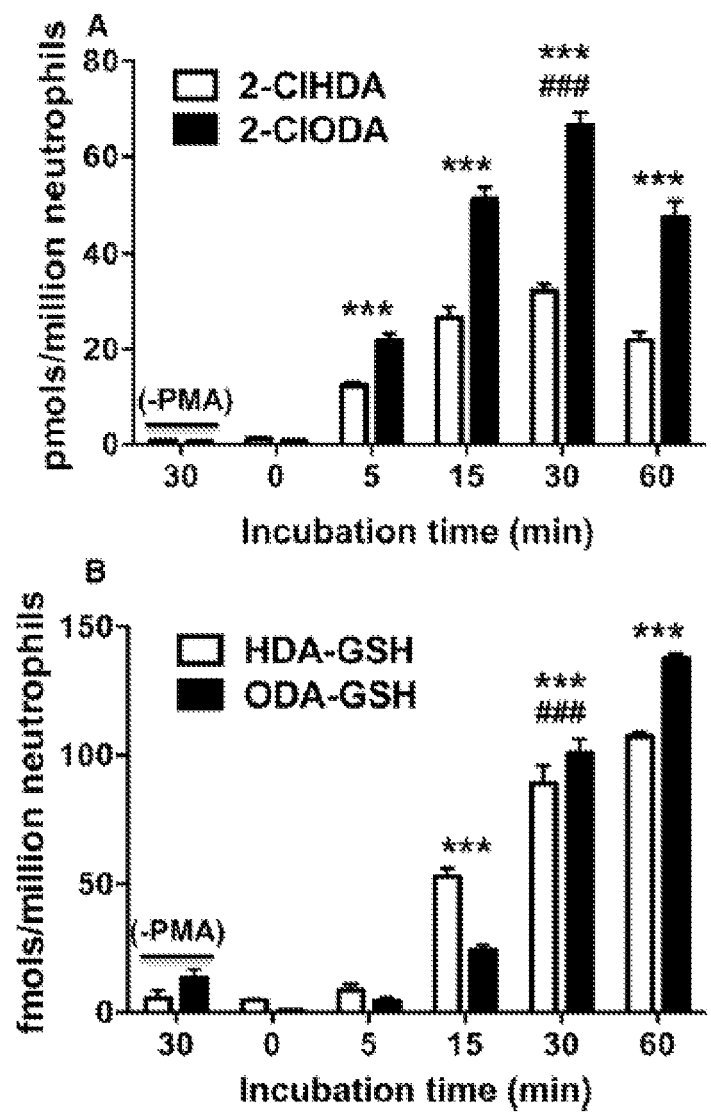
FIGS. 8A-B

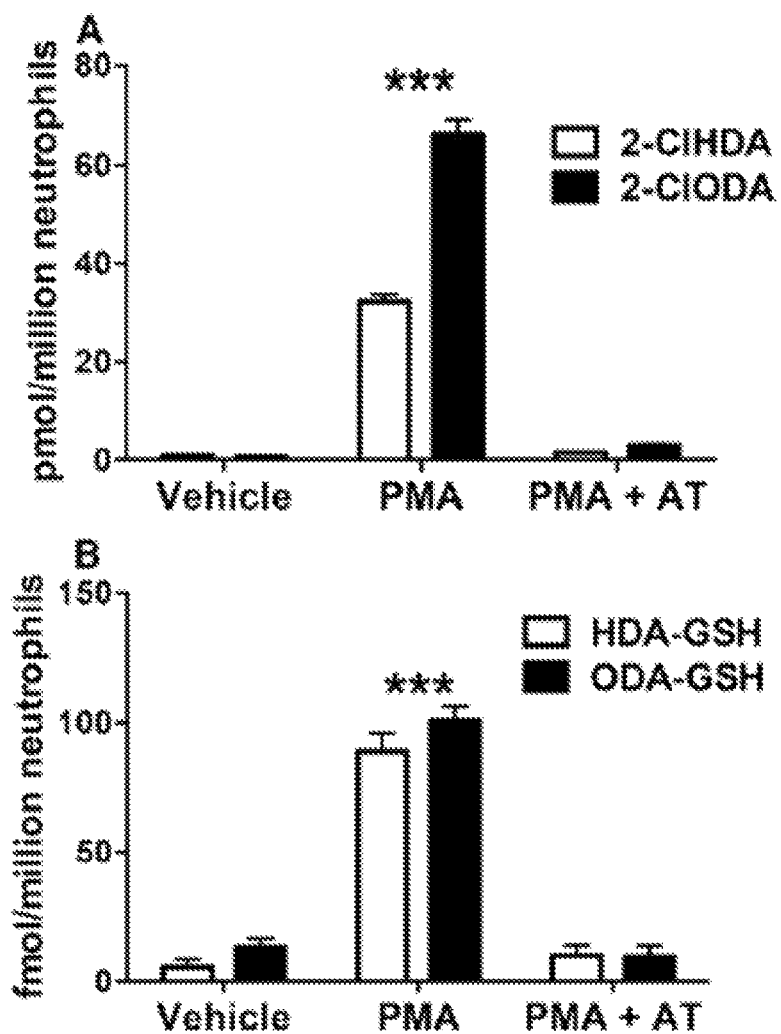
FIGS. 9A-B

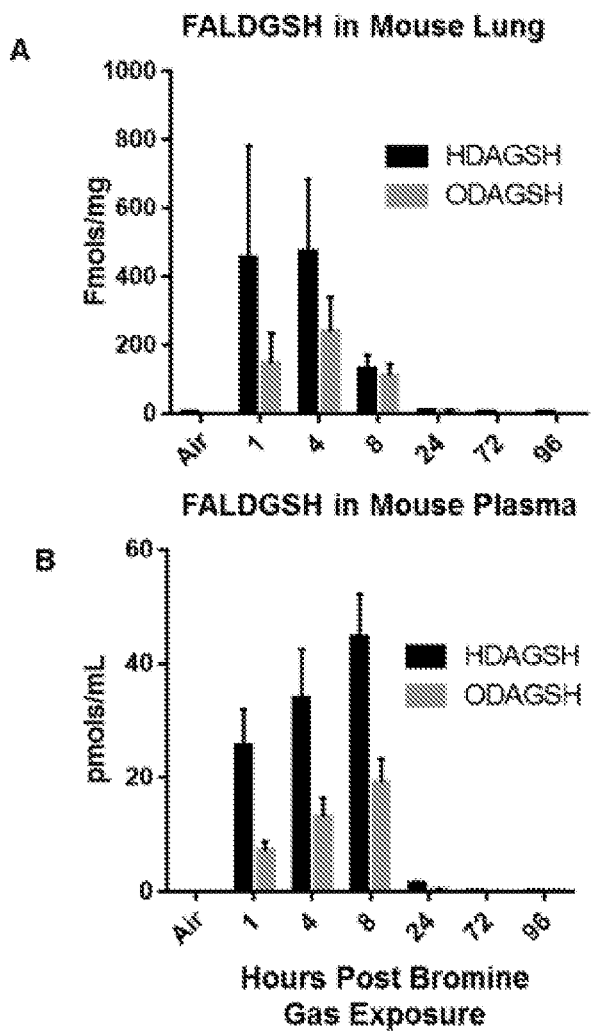
FIG. 10A-B
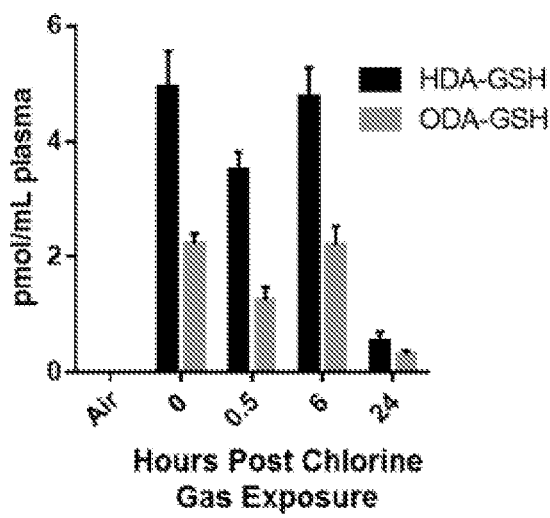
FIG. 11

FIG. 12A-B

DIAGNOSIS OF LEUKOCYTE-MEDIATED DISEASE AND HALOGEN GAS EXPOSURE

This application is a national phase application under 35 U.S.C. § 371 of International Application No. PCT/US2016/013834, filed Jan. 19, 2016, which claims benefit of priority to U.S. Provisional Application Ser. No. 62/106,049, filed Jan. 21, 2015, the entire contents of each of which are hereby incorporated by reference.

BACKGROUND

1. Field

The disclosure relates to the fields of medicine, pathology, biochemistry and cell biology. In particular, the disclosure relates to identification and use of glutathione adducts of 2-halofatty aldehydes (FALD-GSH) for leukocyte disease and halogen gas exposure.

2. Related Art

For halogen gas exposure there are currently no known biomarkers on the market. The same is true for some eosinophil-driven diseases. For example for eosinophilic esophagitis (EE), the only diagnostic tool is taking a biopsy of the esophagitis, followed by obtaining microscopic evidence of eosinophils in a high powered field. The advantage of a biomarker in a disease such as EE would be to avoid a surgical procedure that requires removing part of the esophagus for pathology microscopic evaluation, sometimes only to find that no disease is present. Other eosinophil-driven conditions that could benefit from improved diagnostics include other gastro-esophageal disease, parasitic infections, sepsis, atherosclerosis, and asthma.

SUMMARY

Thus, the present disclosure provides methods of diagnosing a subject as having or being at risk of developing a leukocyte-mediated disease (LMD) comprising (a) detecting the level of glutathione adducts of 2-halofatty aldehydes (FALD-GSH) in a sample; (b) comparing the amount of FALD-GSH with a control or standard reflective of diseased and/or healthy levels of FALD-GSH; and (c) diagnosing the subject as having or being at risk of developing LMD if the level of FALD-GSH in the sample is higher than the control or standard.

The sample may be blood, plasma, serum, sputum, urine, nasal swab, or ear wax. The subject may be suspected of having LMD, may exhibit one or more symptoms of LMD, or may not exhibit a symptom of LMD. The method may further comprise obtaining the sample from the subject. Detecting may comprises (i) mass spectrometry and/or high performance liquid chromatograph (HPLC), or (ii) binding of an antibody to FALD-GSH, such as where an antibody binding to FALD-GSH is employed in immunoprecipitation, Western blot or ELISA. In a particular embodiment, HPLC and mass spectrometry are used in combination.

The method may further comprise performing steps (a) and (b) at a second time point to determine progression of LMD or to determine the efficacy of an intervening treatment. The method may further comprise treating the subject if LMD is diagnosed. The LMD may be selected from the group consisting of asthma, sepsis, atherosclerosis, myocardial infarction, eosinophil and neutrophil mediated disease. The standard or control may comprise detected labeled FALD-GSH. The glutathione adduct may be an adduct of 2-bromofatty aldehyde or 2-chlorofatty aldehyde. The glutathione adduct may be hexadecanal glutathione or octadecanal glutathione.

In another embodiment, there is provided a method of diagnosing a subject as having been exposed to a halogen comprising (a) detecting the level of glutathione adducts of 2-halofatty aldehydes (FALD-GSH) in a sample; (b) comparing the amount of FALD-GSH with a control or standard reflective of levels of FALD-GSH from exposed and/or unexposed individuals; and (c) diagnosing the subject as having been exposed to a halogen if the level of FALD-GSH in the sample is higher than the control or standard.

The sample may be blood, plasma, serum, sputum, urine, nasal swab, or ear wax. The subject may be suspected of having been exposed to a halogen, may exhibit one or more symptoms of being exposed to a halogen, or may not exhibit a symptom of being exposed to a halogen. The method may further comprise obtaining the sample from the subject. Detecting comprises (i) mass spectrometry and/or high performance liquid chromatograph (HPLC), or (ii) binding of an antibody to FALD-GSH, such as where an antibody binding to FALD-GSH is employed in immunoprecipitation, Western blot or ELISA. In a particular embodiment, HPLC and mass spectrometry are used in combination.

The method may further comprise performing steps (a) and (b) at a second time point to determine continued exposure to a halogen or to determine the efficacy of an intervening treatment. The method may further comprise treating the subject if halogen exposure is diagnosed. The halogen may be is selected from chlorine, bromine, iodine, and fluorine. The standard or control comprises detected labeled FALD-GSH. The glutathione adduct may be an adduct of 2-bromofatty aldehyde or 2-chlorofatty aldehyde. The glutathione adduct may be hexadecanal glutathione or octadecanal glutathione.

It is contemplated that any embodiment discussed in this specification can be implemented with respect to any method or composition of the disclosure, and vice versa. Furthermore, compositions of the disclosure can be used to achieve methods of the disclosure.

The use of the word "a" or "an" in the claims and/or the specification may mean "one," but it is also consistent with the meaning of "one or more," "at least one," and "one or more than one."

The phrase "one or more" as found in the claims and/or the specification is defined as 1, 2, 3, 4, 5, 6, 7, 8, 9, 10, or more.

Throughout this application, the terms "about" and "approximately" indicate that a value includes the inherent variation of error for the device, the method being employed to determine the value, or the variation that exists among the study subjects. In one non-limiting embodiment the terms are defined to be within 10%, preferably within 5%, more preferably within 1%, and most preferably within 0.5%.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The disclosure may be better understood by reference to one or more of these drawings in combination with the detailed description of specific embodiments presented herein.

FIGS. 1A-B. TLC separation of reaction products from incubations of 2-ClHDA with GSH. GSH (10 mM) was incubated with 2-ClHDA or HDA (20 mM) in the presence or absence of NEM (15 mM) for 4 h. Reaction products were resolved by silica TLC, and were visualized by either ninhydrin staining (FIG. 1A) or DNPH staining (FIG. 1B).

FIGS. 2A-D. ESI-MS of TLC-purified 2-ClHDA adduct with GSH. The purity and stability of the TLC-purified reaction product from 2-ClHDA incubations with GSH (HDA-GSH) were confirmed by TLC and ninhydrin staining (FIG. 2A). Lanes 1 and 2 show TLC analysis of the reaction products before and after TLC-purification, respectively. Purified reaction product was analyzed by positive ion (FIG. 2B) and negative ion (FIG. 2C) ESI-MS by direct infusion. (FIG. 2D) Putative molecular structure of the reaction product from 2-ClHDA and GSH reactions (HDA-GSH).

FIGS. 4A-C. ESI-MS and MS/MS analysis of DNPH-HDA-GSH. HDA-GSH was derivatized with DNPH and analyzed by direct infusion in positive ion mode. The $[M+H]^+$ of the derivatized product was detected, m/z 726.19 (FIG. 4A), which supports a hydrazone bond formation between DNPH and HDA-GSH and structure shown in (FIG. 4C). MS/MS analysis of the $[M+H]^+$ ion at m/z 726.19 is shown in (FIG. 4B), and the associated table provides likely fragmentation ion assignments.

FIGS. 8A-B. Time course of α-ClFALD and FALD-GSH accumulation in PMA-activated human neutrophils. Isolated primary human neutrophils ($1 \times 10^6$) were incubated in the presence and absence of 200 nM PMA at 37° C. for indicated time intervals. 2-ClHDA and 2-ClODA (FIG. 8A) as well as HDA-GSH and ODA-GSH (FIG. 8B) were quantitated by GC-MS and LC-MS/MS, respectively. n=3 for each treatment. *** indicates $p<0.001$ for comparisons of each FALD-GSH molecular species at indicated time points compared those at t=0. ### indicates $p<0.001$ for comparisons of each FALD-GSH molecular species following 30 min incubations in the presence and absence of PMA.

FIGS. 9A-B. AT inhibition of α-ClFALD and FALD-GSH adduct production in human neutrophils. Isolated primary human neutrophils ($1 \times 10^6$) were incubated in the presence and absence of 200 nM PMA as well as the presence and absence of AT at 37° C. for 30 min. 2-ClHDA and 2-ClODA (FIG. 9A) as well as HDA-GSH and ODA-GSH (FIG. 9B) were quantitated by GC-MS and LC-MS/MS, respectively. n=3 for each treatment. *** indicates $p<0.001$ for both molecular species when compared to the same molecular species in either vehicle control or PMA+AT as assessed by ANOVA with Tukey's post hoc test.

FIGS. 10A-B. Mouse Lung/Plasma Analysis—Bromine Exposure.

FIG. 11. Mouse Plasma Analysis—Chlorine Exposure.

DETAILED DESCRIPTION

The disclosure relates to the use of recently discovered adducts formed from the reaction of glutathione with 2-halofatty aldehydes as plasma biomarkers of leukocyte-mediated disease and halogen gas exposure. 2-halofatty aldehydes are produced by activated leukocytes (Thukkani et al., 2003, 2005) as well as during halogen gas exposure. The inventors recently discovered that these aldehydes are chemically modified by nucleophilic attack by glutathione (GSH) leading to glutathione adducts of these aldehydes (FALD-GSH). FALD-GSH accumulates when leukocytes are activated and are blood borne. FALD-GSH accumulation in blood and or sputum can be an indicator of pro-inflammatory leukocyte mediated disease as well as halogen gas exposure.

The inventors have synthesized this adduct as well as a stable isotope labeled adduct, which is essential for the quantification of this adduct. The adduct can be quantified by high performance liquid chromatography with detection by electrospray ionization mass spectrometry using a method that the inventors have developed. Alternative detection techniques for FALD-GSH include using antibodies to this FALD-GSH, which will make detection of these compounds facile using ELISA assays. FALD-GSH is produced in greater quantities when 2-bromofatty aldehyde is the adducted 2-halofatty aldehyde.

Figure 15:
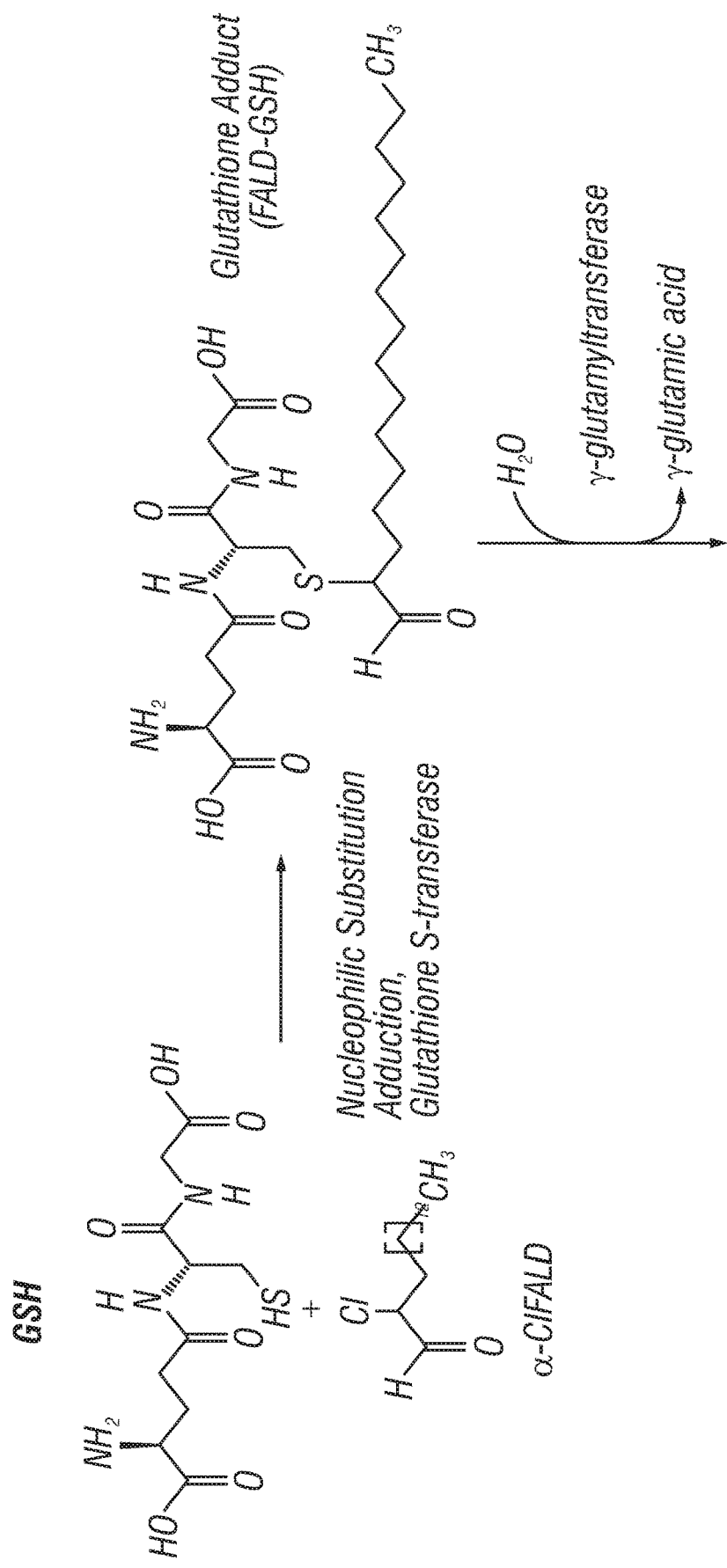
FIG. 15. Glutathione Metabolites.
Figure 15:
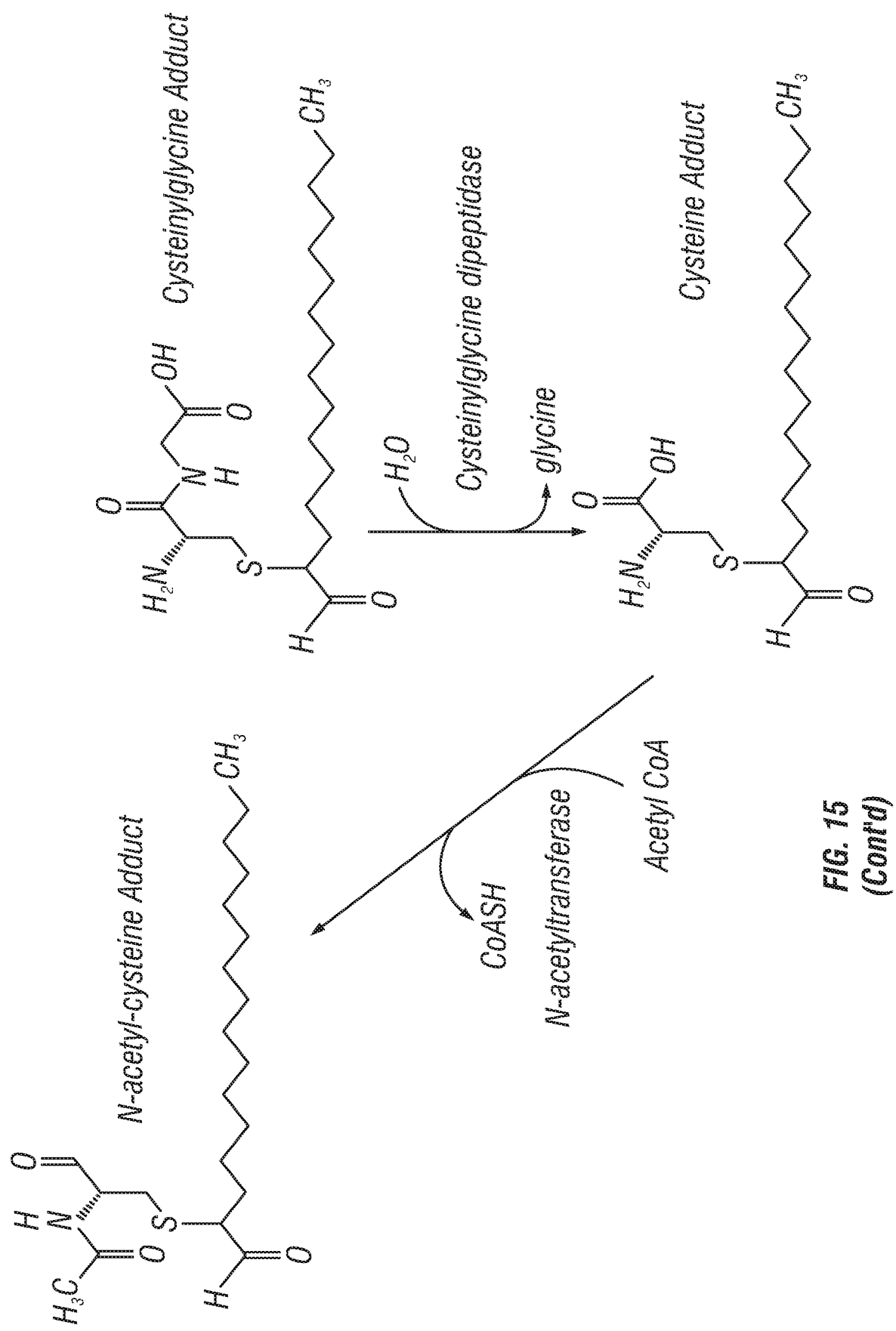

Since 2-bromofatty aldehyde is a specific product of activated eosinophils (Albert et al., 2003), it is predicted that high levels of FALD-GSH in plasma or tissue will be of great diagnostic value for the detection of eosinophil-related diseases such as asthma and gastrointestinal eosinophilic-related diseases (including eosinophilic esophagitis). The inventors also have shown that plasma levels of FALD-GSH are increased in both chlorine and bromine exposed mice. One day after exposure, plasma levels of FALD-GSH in these mice are decreased, indicating there may be additional biomarkers that are metabolites of FALD-GSH that also could be exploited. These metabolites include FALD-cysteine-glycine, FALD-cysteine, and FALD-N-acetyl cysteine. These metabolites are logical based on the mercapturate metabolic pathway (Cooper and Hanigan, 2010; FIG. 15).

These and other aspects of the disclosure are described in detail below.

I. MEDICAL CONDITIONS OF RELEVANCE

In accordance with this disclosure, the inventors propose new diagnostic assays for assessing eosinophilic-mediated abnormalities, and possibly for monocyte- and neutrophil-driven disease. The following are exemplary but non-limiting conditions to which the assays may be applied.

A. Asthma

Asthma is a common chronic inflammatory disease of the airways characterized by variable and recurring symptoms, reversible airflow obstruction and bronchospasm. Common symptoms include wheezing, coughing, chest tightness, and shortness of breath.

Asthma is thought to be caused by a combination of genetic and environmental factors. Its diagnosis is usually based on the pattern of symptoms, response to therapy over time and spirometry. It is clinically classified according to the frequency of symptoms, forced expiratory volume in one second (FEV1), and peak expiratory flow rate. Asthma may also be classified as atopic (extrinsic) or non-atopic (intrinsic) where atopy refers to a predisposition toward developing type 1 hypersensitivity reactions.

Treatment of acute symptoms is usually with an inhaled short-acting beta-2 agonist (such as salbutamol) and oral corticosteroids. In very severe cases, intravenous corticosteroids, magnesium sulfate, and hospitalization may be required. Symptoms can be prevented by avoiding triggers, such as allergens and irritants, and by the use of inhaled corticosteroids. Long-acting beta agonists (LABA) or anti-leukotriene agents (arachidonate 5-lipoxygenase inhibitors or $CysLT_1$ antagonists) may be used in addition to inhaled corticosteroids if asthma symptoms remain uncontrolled. The occurrence of asthma has increased significantly since the 1970s. In 2011, 235-300 million people globally were diagnosed with asthma, and it caused 250,000 deaths.

Asthma is characterized by recurrent episodes of wheezing, shortness of breath, chest tightness, and coughing. Sputum may be produced from the lung by coughing but is often hard to bring up. During recovery from an attack, it may appear pus-like due to high levels of white blood cells called eosinophils. Symptoms are usually worse at night and in the early morning or in response to exercise or cold air. Some people with asthma rarely experience symptoms, usually in response to triggers, whereas others may have marked and persistent symptoms.

1. Associated Conditions

A number of other health conditions occur more frequently in those with asthma, including gastro-esophageal reflux disease (GERD), rhinosinusitis, and obstructive sleep apnea. Psychological disorders are also more common, with anxiety disorders occurring in between 16-52% and mood disorders in 14-41%. However, it is not known if asthma causes psychological problems or if psychological problems lead to asthma. Those with asthma, especially if it is poorly controlled, are at high risk for radiocontrast reactions.

2. Causes

Asthma is caused by a combination of complex and incompletely understood environmental and genetic interactions. These factors influence both its severity and its responsiveness to treatment. It is believed that the recent increased rates of asthma are due to changing epigenetics (heritable factors other than those related to the DNA sequence) and a changing living environment.

Environmental. Many environmental factors have been associated with asthma's development and exacerbation including allergens, air pollution, and other environmental chemicals. Smoking during pregnancy and after delivery is associated with a greater risk of asthma-like symptoms. Low air quality from factors such as traffic pollution or high ozone levels, has been associated with both asthma development and increased asthma severity. Exposure to indoor volatile organic compounds may be a trigger for asthma; formaldehyde exposure, for example, has a positive association. Also, phthalates in certain types of PVC are associated with asthma in children and adults. There is an association between acetaminophen (paracetamol) use and asthma. The majority of the evidence does not; however, support a causal role. A 2014 review found that the association disappeared when respiratory infections were taken into account. Use by a mother during pregnancy is also associated with an increased risk.

Asthma is associated with exposure to indoor allergens. Common indoor allergens include: dust mites, cockroaches, animal dander, and mold. Efforts to decrease dust mites have been found to be ineffective. Certain viral respiratory infections, such as respiratory syncytial virus and rhinovirus, may increase the risk of developing asthma when acquired as young children. Certain other infections, however, may decrease the risk.

Hygiene. The hygiene hypothesis attempts to explain the increased rates of asthma worldwide as a direct and unintended result of reduced exposure, during childhood, to non-pathogenic bacteria and viruses. It has been proposed that the reduced exposure to bacteria and viruses is due, in part, to increased cleanliness and decreased family size in modern societies. Exposure to bacterial endotoxin in early childhood may prevent the development of asthma, but exposure at an older age may provoke bronchoconstriction. Evidence supporting the hygiene hypothesis includes lower rates of asthma on farms and in households with pets.

Use of antibiotics in early life has been linked to the development of asthma. Also, delivery via caesarean section is associated with an increased risk (estimated at 20-80%) of asthma—this increased risk is attributed to the lack of healthy bacterial colonization that the newborn would have acquired from passage through the birth canal. There is a link between asthma and the degree of affluence.

Genetic. Family history is a risk factor for asthma, with many different genes being implicated. If one identical twin is affected, the probability of the other having the disease is approximately 25%. By the end of 2005, 25 genes had been associated with asthma in six or more separate populations, including GSTM1, IL-10, CTLA-4, SPINK5, LTC4S, IL-4R and ADAM33, among others. Many of these genes are related to the immune system or modulating inflammation. Even among this list of genes supported by highly replicated studies, results have not been consistent among all populations tested. In 2006 over 100 genes were associated with asthma in one genetic association study alone; more continue to be found.

Some genetic variants may only cause asthma when they are combined with specific environmental exposures. An example is a specific single nucleotide polymorphism in the CD14 region and exposure to endotoxin (a bacterial product). Endotoxin exposure can come from several environmental sources including tobacco smoke, dogs, and farms. Risk for asthma, then, is determined by both a person's genetics and the level of endotoxin exposure.

Medical conditions. A triad of atopic eczema, allergic rhinitis and asthma is called atopy. The strongest risk factor for developing asthma is a history of atopic disease; with asthma occurring at a much greater rate in those who have either eczema or hay fever. Asthma has been associated with Churg-Strauss syndrome, an autoimmune disease and vasculitis. Individuals with certain types of urticaria may also experience symptoms of asthma.

There is a correlation between obesity and the risk of asthma with both having increased in recent years. Several factors may be at play including decreased respiratory function due to a buildup of fat and the fact that adipose tissue leads to a pro-inflammatory state.

Beta blocker medications such as propranolol can trigger asthma in those who are susceptible. Cardioselective beta-blockers, however, appear safe in those with mild or moderate disease. Other medications that can cause problems in same are ASA, NSAIDs, and angiotensin-converting enzyme inhibitors. COX-2 inhibitors do not appear to be a concern.

Exacerbation. Some individuals will have stable asthma for weeks or months and then suddenly develop an episode of acute asthma. Different individuals react to various factors in different ways. Most individuals can develop severe exacerbation from a number of triggering agents. Some factors that can lead to exacerbation of asthma include dust, animal dander (especially cat and dog hair), cockroach allergens and mold. Perfumes are a common cause of acute attacks in women and children. Both viral and bacterial infections of the upper respiratory tract can worsen the disease. Psychological stress may worsen symptoms—it is thought that stress alters the immune system and thus increases the airway inflammatory response to allergens and irritants.

3. Pathophysiology

Asthma is the result of chronic inflammation of the airways which subsequently results in increased contractability of the surrounding smooth muscles. This among other factors leads to bouts of narrowing of the airway and the classic symptoms of wheezing. The narrowing is typically reversible with or without treatment. Occasionally the airways themselves change. Typical changes in the airways include an increase in eosinophils and thickening of the lamina reticularis. Chronically the airways' smooth muscle may increase in size along with an increase in the numbers of mucous glands. Other cell types involved include: T lymphocytes, macrophages, and neutrophils. There may also be involvement of other components of the immune system including: cytokines, chemokines, histamine, and leukotrienes among others.

4. Diagnosis

While asthma is a well recognized condition, there is not one universal agreed upon definition. It is defined by the Global Initiative for Asthma as "a chronic inflammatory disorder of the airways in which many cells and cellular elements play a role. The chronic inflammation is associated with airway hyper-responsiveness that leads to recurrent episodes of wheezing, breathlessness, chest tightness and coughing particularly at night or in the early morning. These episodes are usually associated with widespread but variable airflow obstruction within the lung that is often reversible either spontaneously or with treatment."

There is currently no precise test with the diagnosis typically based on the pattern of symptoms and response to therapy over time. A diagnosis of asthma should be suspected if there is a history of: recurrent wheezing, coughing or difficulty breathing and these symptoms occur or worsen due to exercise, viral infections, allergens or air pollution. Spirometry is then used to confirm the diagnosis. In children under the age of six the diagnosis is more difficult as they are too young for spirometry.

Spirometry. Spirometry is recommended to aid in diagnosis and management. It is the single best test for asthma. If the FEV1 measured by this technique improves more than 12% following administration of a bronchodilator such as salbutamol, this is supportive of the diagnosis. It however may be normal in those with a history of mild asthma, not currently acting up. As caffeine is a bronchodilator in people with asthma, the use of caffeine before a lung function test may interfere with the results. Single-breath diffusing capacity can help differentiate asthma from COPD. It is reasonable to perform spirometry every one or two years to follow how well a person's asthma is controlled.

Others. The methacholine challenge involves the inhalation of increasing concentrations of a substance that causes airway narrowing in those predisposed. If negative it means that a person does not have asthma; if positive, however, it is not specific for the disease. Other supportive evidence includes: a ≥20% difference in peak expiratory flow rate on at least three days in a week for at least two weeks, a ≥20% improvement of peak flow following treatment with either salbutamol, inhaled corticosteroids or prednisone, or a ≥20% decrease in peak flow following exposure to a trigger. Testing peak expiratory flow is more variable than spirometry, however, and thus not recommended for routine diagnosis. It may be useful for daily self-monitoring in those with moderate to severe disease and for checking the effectiveness of new medications. It may also be helpful in guiding treatment in those with acute exacerbations.

B. Eosiniphilic Esophagitis

Eosinophilic esophagitis (EE) is an increasingly recognized eosinophilic gastrointestinal disease (EGID). It accounts for about 50% of dysphagia and food impaction. It has been proposed that food allergy is the underlying etiology of EE. Recent translational studies show that skin prick tests (SPTs) are currently the best available tool to identify the triggering food allergens and >90% of patients respond to dietary interventions, thus supporting a role for humoral (IgE) and/or cell-mediated food allergy. In addition, esophageal mast cells are significantly increased in EE compared to normal controls and gastroesophageal reflux disease (GERD). Notably, of various dysregulated genes identified by DNA microarray studies, five mast cell genes were highly induced, including the high-affinity IgE receptor (FcεRI) and mast cell tryptase-α. However, the role of IgE-mediated mast cell (or basophil) responses in the esophageal inflammatory cascade in EE remains uncertain, as noted by the fact that RAST testing alone shows poor specificity for identifying offending foods. To date, no studies have prospectively examined the role of IgE in the esophageal microenvironment associated with EE.

EE is a disorder of the esophagus characterized by esophageal and/or upper gastrointestinal tract symptoms in association with esophageal mucosal biopsy specimens containing high amount of intraepithelial eosinophils within the esophageal squamous epithelium or deeper tissue levels and normal pH monitoring. EE affects males more than females, and the diagnosis is typically made in adults during the third and fourth decades of life, although it may be diagnosed at a later age. In children, the diagnosis is made after infancy and through adolescence with no recognized peak age of onset. Symptoms may include chest pain, heartburn, dysphagia, food impaction and a lack of responsiveness to acid reducing medications. Treatment of EE involves either corticosteroids or elemental diet and not surgery.

Standard of care for EE patients includes initial esophageal endoscopy with biopsy to determine the numbers of epithelial eosinophils (>5/hpf being diagnostic). Since consequences of chronic eosinophilic inflammation in EE can include esophageal remodeling with subsequent esophageal narrowing, trachealization and strictures, therapeutic efforts are typically devoted toward inducing clinical as well as histological remission. While overall relatively safe, esophageal endoscopy entails procedural risks, is expensive, time consuming and is limited to procuring a 3 mm sample.

To date, no serological, stool or non-invasive tests have provided durable results correlating histological evidence of disease progression or remission in EE. Presently, the state of esophageal inflammation in patients with EE can only be assessed with an invasive endoscopy. Although the cost-benefit ratio is unknown, repeated endoscopies with biopsies are the best test tool date to assess disease status and response to treatment.

To address this issue, an Esophageal String Test or EST, such as the Enterotest®. a string-based test first used for detection of Giardia infections, can be used in its native form to assess esophageal inflammation at both the protein and mRNA levels and may potentially be used to monitor disease activity. The EST may offer a minimally invasive method to assess the presence of inflammation associated with active disease.

1. Eosinophilic Esophagitis and Food Allergies

Food allergic diseases affect between 4-6% of children in the United States per year. During the last decade, an increasing number of children developed a new manifestation of food allergy termed eosinophilic esophagitis (EE). Several lines of evidence support a close relationship of EE with food allergic diseases. First, skin prick testing (SPT), a reliable indicator of IgE-mediated food reactions, correlates consistently with esophageal inflammation in EE. Second, patients with EE often associate symptoms following the ingestion of specific foods. Furthermore, specific elimination of those foods and/or foods identified by SPTs leads to clinicopathological remission in EE. Third, mucosal biopsies from patients with EE demonstrate significantly increased numbers of mucosal mast cells compared to those from patients with gastroesophageal reflux disease (GERD) or normal subjects, suggesting their participation in the pathogenesis of this disease. Finally, previous work suggests that patients with eosinophilic gastrointestinal diseases (EGIDs) and food allergy demonstrate increased expression of CD23 on intestinal epithelial cells and in stool samples. While the precise role of CD23 in food allergic responses is not certain, recent studies suggest that the human CD23a isoform participates as a bidirectional transporter of both free IgE and IgE/antigen complexes, and can potentially deliver IgE and its bound allergen across intestinal epithelial cells to induce mast cell activation. Taken together, these observations provide strong evidence supporting a role of food allergic responses (including those mediated by IgE) in the pathogenesis of EE.

2. Diagnostic Criteria for Eosinophilic Esophagitis

The recent emergence of EE is emphasized by the fact that diagnostic criteria have only recently been established. Clinically, EE is characterized by symptoms including abdominal pain, regurgitation, feeding intolerance, food impaction and dysphagia. Histologically, esophageal biopsies contain large numbers of intraepithelial eosinophils (≥15 eosinophils/high power field), often with eosinophil microabscesses and luminal layering. These findings are unresponsive to acid blockade, e.g., proton pump inhibition, but do respond to elimination (or elemental) diets and corticosteroids. This disease does not affect the columnar epithelium of the stomach or small intestine. Thus, when a patient has persistent symptoms that are associated with esophageal epithelial eosinophilia and normal gastric and duodenal mucosa, and gastroesophageal reflux (GERD) and other causes of eosinophilia have been ruled out, the diagnosis of EE can be made with confidence. The importance of clear diagnostic criteria is emphasized by the fact that many patients are now receiving the diagnosis of EE based on histological findings alone, without proper investigations to exclude other causes of esophageal eosinophilia.

3. Pathogenesis of Eosinophilic Esophagitis

Although a number of factors relate food allergic responses to EE, the exact mechanisms defining the pathogenesis of EE remain uncertain. Current paradigms of potential mechanisms underlying EE address several different pathways including, the role of IgE in EE, identifying the mechanisms of squamous eosinophilia, and defining whether the associated phenotype of patients is predominantly Th1 or Th2. A few translational studies have addressed the participation of IgE-mediated immediate hypersensitivity responses in EE. Increased numbers of mast cells, CD23 expression on intestinal epithelial cells, and historical evidence of other IgE-mediated allergic diseases, provide circumstantial evidence supporting a role for IgE-mediated responses in EE. Alternatively, not all patients have elevated total or specific IgE, show evidence of atopic disease, or have increased mast cells in their esophageal tissue. Typically, patients do not complain of immediate reactions associated with the ingestion of candidate foods, and do not present with systemic allergic symptoms involving other organs such as the lung or skin, although EE has been referred to by some as "asthma or eczema of the esophagus."

A translational study focused on one potential mechanism that drives eosinophils into the esophageal squamous epithelium. A DNA microarray study showed that the eosinophil-specific chemoattractant eotaxin-3 (CCL26) was the most highly up-regulated gene in the squamous epithelium from biopsies of patients with EE compared to those with GERD and those with normal mucosa. In this report, studies using eotaxin receptor CCR3-deficient (knockout) mice confirmed that esophageal eosinophilia, in an IgE-dependent intranasal allergen model, was dependent on the presence of CCR3 for eosinophil recruitment to the esophagus. Finally, 32.1% of EE patients compared to 22.4% of non-EE matched subjects in this study had a single nucleotide polymorphism (SNP)+2,496 T→G in the eotaxin-3 gene that was associated with disease susceptibility. Thus, eotaxin-3 remains the only biomarker to date associated with EE. However, since only a limited percentage of patients possessed this eotaxin-3 SNP, it is likely that other relevant biomarkers will be identified.

Basic and clinical studies suggest that the preponderance of inflammatory responses associated with EE is of a Th2 phenotype. As demonstrated in murine models utilizing IL-5 and eotaxin-1 null mice, esophageal eosinophilia is dependent on IL-5 expression and partially dependent on eotaxin-1. Histological staining of affected esophageal epithelium shows increased IL-5 staining and a recent small clinical series showed that anti-IL-5 antibody leads to the resolution of clinical and histological findings in some EE patients. While food allergen-induced responses leading to overexpression of eotaxin-3 by the squamous epithelium in the esophagus are likely involved in the Th2 inflammatory cascade, the precise pathogenesis of esophageal eosinophilia in EE has yet to be established. To date, eotaxin-3 is the only potential biomarker that has been identified for EE.

4. Problems Associated with Care of Patients with EE

While treatments of EE have become well accepted in terms of the use of nutritional elimination diets, including elemental diets, and corticosteroid administration, the precise treatment endpoints are much less clear. For instance, some clinicians treat to resolve only symptoms, while others treat to induce both clinical and histological remission, i.e. treat to decrease numbers of esophageal eosinophils. This decision is often shaped by the reluctance to have patients undergo repeated esophagogastroduodenoscopy (endoscopy) and biopsies, and by uncertainty about the natural history and incidence of long-term sequelae of chronic esophageal eosinophilia that include esophageal remodeling, subepithelial fibrosis and narrowing. Those who feel that chronic esophageal eosinophilia leads to esophageal fibrosis and stricture formation treat patients and perform repeat endoscopy with biopsy to insure that mucosal eosinophilia has resolved. Those who feel that chronic esophageal eosinophilia will not lead to esophageal strictures will treat with symptom relief as the only endpoint and not repeat endoscopy with biopsy. Thus, a significant number of EE patients who never undergo post-treatment sampling of their mucosa may continue to have mucosal disease that could possibly leave them vulnerable to the long-term complications of chronic esophageal eosinophilia. Alternatively, patients may not develop complications, but which patients will or will not develop these complications, how long it might take, and where the complications will develop anatomically are entirely unknown, since the natural history of EE has not been adequately characterized. Thus, the cost-benefit analysis of repeated endoscopies has not been determined.

In this regard, the obvious problem is that the only method currently available to determine the state of esophageal mucosal inflammation is endoscopy with mucosal biopsy. While this procedure is relatively safe overall, several downsides do exist including the potential complications of conscious sedation or general anesthesia (hypoxia, allergic reactions to the medications, airway compromise) and risks of the procedure itself (esophageal perforation, bleeding and infection). Endoscopy with biopsy is limited in that each biopsy only provides an assessment of <0.001% of the total esophageal surface area. Endoscopy is costly and often is not covered by insurance companies when repeated as described above. It is also important to recognize that while EE is currently a recognized disease amongst most clinicians, an ICD-9 code for EE does not yet exist. This lack of "certification" of EE has created administrative confusion in terms of how to pay for endosocopy. Finally, endoscopy results in lost time from school or work. Other proposed methods to analyze the esophageal mucosa include monitoring symptoms, radiological studies, and serum or stool analyses. It is a well-recognized fact that symptoms do not necessarily correlate with evidence of histological activity. To date, no serological or stool analysis has provided reliable and durable findings that correlate with and are consistently predictive of histological evidence of disease remission or progression. Aside from a recent study showing correlations for measurements of absolute eosinophil counts, plasma EDN and eotaxin-3 levels with disease status, preliminary studies measuring eosinophil granule cationic proteins in the serum of affected patients have failed to find significant correlations with disease activity. Taken together, these findings indicate that a minimally invasive, inexpensive, safe, reliable and accurate method for direct measurement of esophageal inflammation is needed for initial diagnosis and post-treatment management of patients with EE.

C. Atherosclerosis

1. Definition and Characteristics

Atherosclerosis (also known as arteriosclerotic vascular disease or ASVD) is a specific form of arteriosclerosis in which an artery wall thickens as a result of invasion and accumulation of white blood cells (WBCs). The accumulation of the WBCs is termed "fatty streaks" early on because of appearance being similar to that of marbled steak. These accumulations contain both living, active WBCs (producing inflammation) and remnants of dead cells, including cholesterol and triglycerides. The remnants eventually include calcium and other crystallized materials, within the outermost and oldest plaque. The "fatty streaks" reduce the elasticity of the artery walls. However, they do not affect blood flow for decades, because the artery muscular wall enlarges at the locations of plaque. The wall stiffening may eventually increase pulse pressure; widened pulse pressure is one possible result of advanced disease within the major arteries.

Atherosclerosis is therefore a syndrome affecting arterial blood vessels due to a chronic inflammatory response of WBCs in the walls of arteries. This is promoted by low-density lipoproteins (LDL, plasma proteins that carry cholesterol and triglycerides) without adequate removal of fats and cholesterol from the macrophages by functional high-density lipoproteins (HDL). It is commonly referred to as a "hardening" or furring of the arteries. It is caused by the formation of multiple atheromatous plaques within the arteries, which are divided into three distinct components:

the atheroma, which is the nodular accumulation of a soft, flaky, yellowish material at the center of large plaques, composed of macrophages nearest the lumen of the artery underlying areas of cholesterol crystals calcification at the outer base of older or more advanced lesions Atherosclerosis is a chronic disease that remains asymptomatic for decades. Atherosclerotic lesions, or atherosclerotic plaques, are separated into two broad categories: Stable and unstable (also called vulnerable). The pathobiology of atherosclerotic lesions is very complicated but generally, stable atherosclerotic plaques, which tend to be asymptomatic, are rich in extracellular matrix and smooth muscle cells, while, unstable plaques are rich in macrophages and foam cells and the extracellular matrix separating the lesion from the arterial lumen (also known as the fibrous cap) is usually weak and prone to rupture. Ruptures of the fibrous cap expose thrombogenic material, such as collagen, to the circulation and eventually induce thrombus formation in the lumen. Upon formation, intraluminal thrombi can occlude arteries outright (e.g. coronary occlusion), but more often they detach, move into the circulation and eventually occluding smaller downstream branches causing thromboembolism. Apart from thromboembolism, chronically expanding atherosclerotic lesions can cause complete closure of the lumen. Chronically expanding lesions are often asymptomatic until lumen stenosis is so severe (usually over 80%) that blood supply to downstream tissue(s) is insufficient, resulting in ischemia.

These complications of advanced atherosclerosis are chronic, slowly progressive and cumulative. Most commonly, soft plaque suddenly ruptures (see vulnerable plaque), causing the formation of a thrombus that will rapidly slow or stop blood flow, leading to death of the tissues fed by the artery in approximately five minutes. This catastrophic event is called an infarction. One of the most common recognized scenarios is called coronary thrombosis of a coronary artery, causing myocardial infarction (a heart attack). The same process in an artery to the brain is commonly called stroke. Another common scenario in very advanced disease is claudication from insufficient blood supply to the legs. Atherosclerosis affects the entire artery tree, but mostly larger, high-pressure vessels such as the coronary, renal, femoral, cerebral, and carotid arteries. These are termed "clinically silent" because the person having the infarction does not notice the problem and does not seek medical help, or when they do, physicians do not recognize what has happened.

2. Causation

The atherosclerotic process is not fully understood. Atherosclerosis is initiated by inflammatory processes in the endothelial cells of the vessel wall in response to retained low-density lipoprotein (LDL) particles.

Lipoproteins in the blood vary in size. Some data suggests that small dense LDL (sdLDL) particles are more prone to pass between the endothelial cells, going behind the cellular monolayer of endothelium. LDL particles and their content are susceptible to oxidation by free radicals, and the risk is higher while the particles are in the wall than while in the bloodstream. However, LDL particles have a half-life of only a couple of days, and their content (LDL particles typically carry 3,000 to 6,000 fat molecules, including: cholesterol, phospholipids, cholesteryl esters, triglycerides & all other fats in the water outside cells, to the tissues of the body) changes with time.

Oxidation mechanisms associated with vascular inflammation have been given considerable attention as a mechanism mediating atherosclerotic lesion formation and propagation. Myeloperoxidase (MPO)-catalyzed oxidation is considered to be a major mechanism mediating human atherosclerotic disease. Monocyte- and macrophage-derived MPO catalyzes the production of HOCl and its conjugate base ($OCl^-$). Multiple MPO-derived oxidation products have been found in human atherosclerotic lesions including chlorotyrosine, nitrotyrosine and α-CIFALD. Of these oxidation products our lab discovered that the sn-1 vinyl ether bond of plasmalogens is oxidized by HOCl resulting in the production of α-CIFALD (33) which led to our finding that α-CIFALD accumulates in human atherosclerotic tissue (31).

Once inside the vessel wall, LDL particles can become more prone to oxidation. Endothelial cells respond by attracting monocyte white blood cells, causing them to leave the blood stream, penetrate into the arterial walls and transform into macrophages. The macrophages' ingestion of oxidized LDL particles triggers a cascade of immune responses which over time can produce an atheroma if HDL removal of fats from the macrophages does not keep up. The immune system's specialized white blood cells (macrophages and T-lymphocytes) absorb the oxidized LDL, forming specialized foam cells. If these foam cells are not able to process the oxidized LDL and recruit HDL particles to remove the fats, they grow and eventually rupture, leaving behind cellular membrane remnants, oxidized materials, and fats (including cholesterol) in the artery wall. This attracts more white blood cells, resulting in a snowballing progression that continues the cycle, inflaming the artery. The presence of the plaque induces the muscle cells of the blood vessel to stretch, compensating for the additional bulk, and the endothelial lining thickens, increasing the separation between the plaque and lumen. This somewhat offsets the narrowing caused by the growth of the plaque, but it causes the wall to stiffen and become less compliant to stretching with each heart beat.

Some researchers believe that atherosclerosis may be caused by an infection of the vascular smooth muscle cells. Chickens, for example, develop atherosclerosis when infected with the Marek's disease herpesvirus. Herpesvirus infection of arterial smooth muscle cells has been shown to cause cholesteryl ester (CE) accumulation, which is associated with atherosclerosis. Cytomegalovirus (CMV) infection is also associated with cardiovascular diseases.

3. Diagnosis

Areas of severe narrowing, stenosis, detectable by angiography, and to a lesser extent "stress testing" have long been the focus of human diagnostic techniques for cardiovascular disease, in general. However, these methods focus on detecting only severe narrowing, not the underlying atherosclerosis disease. As demonstrated by human clinical studies, most severe events occur in locations with heavy plaque, yet little or no lumen narrowing present before debilitating events suddenly occur. Plaque rupture can lead to artery lumen occlusion within seconds to minutes, and potential permanent debility and sometimes sudden death.

Plaques that have ruptured are called complicated plaques. The extracellular matrix of the lesion breaks, usually at the shoulder of the fibrous cap that separates the lesion from the arterial lumen, where the exposed thrombogenic components of the plaque, mainly collagen will trigger thrombus formation. The thrombus then travels downstream to other blood vessels, where the blood clot may partially or completely block blood flow. If the blood flow is completely blocked, cell deaths occur due to the lack of oxygen supply to nearby cells, resulting in necrosis. The narrowing or obstruction of blood flow can occur in any artery within the body. Obstruction of arteries supplying the heart muscle result in a heart attack, while the obstruction of arteries supplying the brain result in a stroke.

Lumen stenosis that is greater than 75% were considered as the hallmark of clinically significant disease in the past because recurring episodes of angina and abnormalities in stress test are only detectable at that particular severity of stenosis. However, clinical trials have shown that only about 14% of clinically debilitating events occur at sites with >75% stenosis. Majority of cardiovascular events that involve sudden rupture of the atheroma plaque do not display any evident narrowing of the lumen. Thus, greater attention has been focused on "vulnerable plaque" from the late 1990's onwards.

Besides the traditional diagnostic methods such as angiography and stress-testing, other detection techniques have been developed in the past decades for earlier detection of atherosclerotic disease. Some of the detection approaches include anatomical detection and physiologic measurement.

Examples of anatomical detection methods include (1) coronary calcium scoring by CT, (2) carotid IMT (intimal media thickness) measurement by ultrasound, and (3) intravascular ultrasound (IVUS). Examples of physiologic measurement methods include (1) lipoprotein subclass analysis, (2) HbA1c, (3) hs-CRP, and (4) homocysteine. Both anatomic and physiologic methods allow early detection before symptoms show up, disease staging and tracking of disease progression. Anatomic methods are more expensive and some of them are invasive in nature, such as IVUS. On the other hand, physiologic methods are often less expensive and safer. But they do not quantify the current state of the disease or directly track progression. In the recent years, ways of estimating the severity of atherosclerotic plaques is also made possible with the developments in nuclear imaging techniques such as PET and SPECT.

D. Sepsis

Sepsis is a serious medical condition characterized by a whole-body inflammatory state caused by infection. Traditionally the term sepsis has been used interchangeably with septicaemia and septicemia ("blood poisoning"). However, these terms are no longer considered synonymous; septicemia is considered a subset of sepsis. Indeed, the inventors have shown (unpublished data) that myeloperoxidase-derived products are increased in a rat model of sepsis, and chlorinated fatty acids are increased in the cecum in the cecal ligation model of rat sepsis.

Symptoms of sepsis are often related to the underlying infectious process. When the infection crosses into sepsis, the resulting symptoms are that of systemic inflammatory response syndrome (SIRS): general inflammation, fever, elevated white blood cell count (leukocytosis), and raised heart rate (tachycardia) and breathing rate (tachypnea). Secondary to the above, symptoms also include flu like chills.

The immunological response that causes sepsis is a systemic inflammatory response causing widespread activation of inflammation and coagulation pathways. This may progress to dysfunction of the circulatory system and, even under optimal treatment, may result in the multiple organ dysfunction syndrome and eventually death.

Sepsis is considered present if infection is highly suspected or proven and two or more of the following systemic inflammatory response syndrome (SIRS) criteria are met:
  heart rate >90 beats per minute
  body temperature <36° C. (96.8° F.) or >38° C. (100.4° F.)
  hyperventilation (high respiratory rate) >20 breaths per minute or, on blood gas, a $P_aCO_2$ less than 32 mm Hg
  white blood cell count <4000 cells/mm$^3$ or >12,000 cells/mm$^3$ (<4×10$^9$ or >12×10$^9$ cells/L), or greater than 10% band forms (immature white blood cells) Consensus definitions however continue to evolve with the latest expanding the list of signs and symptoms of sepsis to reflect clinical bedside experience.

The more critical subsets of sepsis are severe sepsis (sepsis with acute organ dysfunction) and septic shock (sepsis with refractory arterial hypotension). Alternatively, when two or more of the systemic inflammatory response syndrome criteria are met without evidence of infection, patients may be diagnosed simply with "SIRS." Patients with SIRS and acute organ dysfunction may be termed "severe SIRS."

Patients are defined as having "severe sepsis" if they have sepsis plus signs of systemic hypoperfusion; either end organ dysfunction or a serum lactate greater than 4 mmol/dL. Patient are defined as having septic shock if they have sepsis plus hypotension after an appropriate fluid bolus (typically 20 ml/kg of crystaloid). The criteria for diagnosing an adult with sepsis do not apply to infants under one month of age. In infants, only the presence of infection plus a "constellation" of signs and symptoms consistent with the systemic response to infection are required for diagnosis.

The therapy of sepsis rests on antibiotics, surgical drainage of infected fluid collections, fluid replacement and appropriate support for organ dysfunction. This may include hemodialysis in kidney failure, mechanical ventilation in pulmonary dysfunction, transfusion of blood products, and drug and fluid therapy for circulatory failure. Ensuring adequate nutrition, if necessary by parenteral nutrition, is important during prolonged illness.

A problem in the adequate management of septic patients has been the delay in administering therapy after sepsis has been recognized. Published studies have demonstrated that for every hour delay in the administration of appropriate antibiotic therapy there is an associated 7% rise in mortality.

Most therapies aimed at the inflammatory process itself have failed to improve outcome, however drotrecogin alfa (activated protein C, one of the coagulation factors) has been shown to decrease mortality from about 31% to about 25% in severe sepsis. To qualify for drotrecogin alfa, a patient must have severe sepsis or septic shock with an APACHE II score of 25 or greater and a low risk of bleeding. Low dose hydrocortisone treatment has shown promise for septic shock patients with relative adrenal insufficiency as defined by ACTH stimulation testing.

Standard treatment of infants with suspected sepsis consists of supportive care, maintaining fluid status with intravenous fluids, and the combination of a beta-lactam antibiotic (such as ampicillin) with an aminoglycoside such as gentamicin.

E. Myocardial Infarction

Myocardial infarction (MI) or acute myocardial infarction (AMI), commonly known as a heart attack, is the interruption of blood supply to a part of the heart, causing heart cells to die. This is most commonly due to occlusion (blockage) of a coronary artery following the rupture of a vulnerable atherosclerotic plaque, which is an unstable collection of lipids (fatty acids) and white blood cells (especially macrophages) in the wall of an artery. The resulting ischemia (restriction in blood supply) and oxygen shortage, if left untreated for a sufficient period of time, can cause damage or death (infarction) of heart muscle tissue (myocardium). Heart attacks are the leading cause of death for both men and women worldwide.

An MI is a medical emergency which requires immediate medical attention. Treatment attempts to salvage as much myocardium as possible and to prevent further complications, thus the phrase "time is muscle." Oxygen, aspirin, and nitroglycerin may be administered. Morphine was classically used if nitroglycerin was not effective; however, it may increase mortality in the setting of NSTEMI. Coronary intervention (PCI) or fibrinolysis are recommended in those with an STEMI. In people who have multiple blockages and who are relatively stable, or in a few emergency cases, bypass surgery may be an option.

1. Drug Therapies

Thrombolytic therapy improves survival rates in patients with acute myocardial infarction if administered in a timely fashion in the appropriate group of patients. If PCI capability is not available within 90 minutes, then choice is to administer thrombolytics within 12 hours of onset of symptoms in patients with ST-segment elevation greater than 0.1 mV in 2 or more contiguous ECG leads, new left bundle-branch block (LBBB), or anterior ST depression consistent with posterior infarction. Tissue plasminogen activator (t-PA) is preferred over streptokinase as achieving a higher rate of coronary artery patency; however, the key lies in speed of the delivery.

Aspirin has been shown to decrease mortality and re-infarction rates after myocardial infarction. Again, delivery should be immediate, which should be chewed if possible. The treatment should continues indefinitely in the absence of obvious contraindication, such as a bleeding tendency or an allergy. Clopidogrel may be used as an alternative in cases of a resistance or allergy to aspirin (dose of 300 mg), but a higher dose of clopidogrel may have added benefit.

Platelet glycoprotein (GP) IIb/IIIa-receptor antagonist is another therapy in patients with continuing ischemia or with other high-risk features and to patients in whom a percutaneous coronary intervention (PCI) is planned. Eptifibatide and tirofiban are approved for this use, and abciximab also can be used for 12-24 hours in patients with unstable angina or NSTEMI in whom a PCI is planned within the next 24 hours.

Heparin and other anticoagulant agents have an established role as adjunct agents in patients receiving t-PA, but not in patients receiving streptokinase. Heparin is also indicated in patients undergoing primary angioplasty. Low molecular-weight heparins (LMWHs) have been shown to be superior to UFHs in patients with unstable angina or NSTEMI. Bivalirudin, a direct thrombin inhibitor, has shown promise in STEMI if combined with high-dose clopidogrel.

Nitrates have no apparent impact on mortality rate in patients with ischemic syndromes, but they are useful in symptomatic relief and preload reduction, so much so that all patients with acute myocardial infarction are given nitrates within the first 48 hours of presentation, unless contraindicated (i.e., in RV infarction). Beta-blockers may reduce the rates of reinfarction and recurrent ischemia, and thus are administered to patients with MIs unless a contraindication is present.

ACE inhibitors reduce mortality rates after myocardial infarction and thus are administered as soon as possible as long as no contraindications are and the patient remains stable. ACE inhibitors have the greatest benefit in patients with ventricular dysfunction. Continue ACE inhibitors indefinitely after myocardial infarction. Angiotensin-receptor blockers may be used as an alternative in patients who develop adverse effects, such as a persistent cough, although initial trials need to be confirmed.

2. PCI and Other Surgical Intervention

PCI is the treatment of choice in most patients with STEMI, assuming a door to balloon time of less than 90 minutes. PCI provides greater coronary patency (>96% thrombolysis), lower risk of bleeding, and instant knowledge about the extent of the underlying disease. Studies have shown that primary PCI has a mortality benefit over thrombolytic therapy. The choice of primary PCI should be individualized to each patient's presentation and timing. Primary PCI is also the treatment of choice in patients with cardiogenic shock, patients in whom thrombolysis failed, and those with high risk of bleeding or contraindications to thrombolytic therapy.

Emergent or urgent coronary artery graft bypass surgery is indicated in patients in whom angioplasty fails and in patients who develop mechanical complications such as a VSD, LV, or papillary muscle rupture.

F. Halogen Gas Exposure

The halogens or halogen elements are a group in the periodic table consisting of five chemically related elements: fluorine (F), chlorine (Cl), bromine (Br), iodine (I), and astatine (At). The artificially created element 117 (ununseptium) may also be a halogen. In the modern IUPAC nomenclature, this group is known as group 17.

The group of halogens is the only periodic table group that contains elements in all three familiar states of matter at standard temperature and pressure. All of the halogens form acids when bonded to hydrogen. Most halogens are typically produced from minerals or salts. The middle halogens—chlorine, bromine and iodine—are often used as disinfectants. Organobromides are the most important class of flame retardants.

Elemental halogens are generally toxic. The halogens tend to decrease in toxicity towards the heavier halogens. For example, fluorine gas is extremely toxic; breathing fluorine gas at a concentration of 0.1% for several minutes is lethal. Hydrofluoric acid is also toxic, being able to penetrate skin and cause highly painful burns. In addition, fluoride anions are toxic, but not as toxic as pure fluorine. Fluoride can be lethal in amounts of 5 to 10 grams. Prolonged consumption of fluoride above concentrations of 1.5 mg/L is associated with a risk of dental fluorosis, an aesthetic condition of the teeth. At concentrations above 4 mg/L, there is an increased risk of developing skeletal fluorosis, a condition in which bone fractures become more common due to the hardening of bones. Current recommended levels in water fluoridation, a way to prevent dental caries, range from 0.7-1.2 mg/L to avoid the detrimental effects of fluoride while at the same time reaping the benefits. People with levels between normal levels and those required for skeletal fluorosis tend to have symptoms similar to arthritis.

Chlorine gas is highly toxic. Breathing in chlorine at a concentration of 3 parts per million can rapidly cause a toxic reaction. Breathing in chlorine at a concentration of 50 parts per million is highly dangerous. Breathing in chlorine at a concentration of 500 parts per million for a few minutes is lethal. Breathing in chlorine gas is highly painful. Hydrochloric acid is a dangerous chemical.

Pure bromine is somewhat toxic, but less toxic than fluorine and chlorine. One hundred milligrams of bromine are lethal. Bromide anions are also toxic, but less so than bromine. Bromide has a lethal dose of 30 grams.

Iodine is somewhat toxic, being able to irritate the lungs and eyes, with a safety limit of 1 milligram per cubic meter. When taken orally, 3 grams of iodine can be lethal. Iodide anions are mostly nontoxic, but these can also be deadly if ingested in large amounts.

Astatine is very radioactive and thus highly dangerous.

III. ANTIBODIES AS DIAGNOSTIC PROBES

Antibodies may be generated against protein targets in the glutathione adducts of 2-halofatty aldehydes (FALD-GSH) described herein. Antibodies are defined by their binding specificity. Those of skill in the art are well aware of methods by which such antibodies can be made and identified. Assessing the binding specificity/affinity of a given antibody using techniques is also well known to those of skill in the art, thereby permitting one to determine what antibodies fall within the scope of this disclosure.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

Antibodies may be associated with a label or reporter molecule, which is defined here as any moiety which may be detected using an assay. Non-limiting examples of reporter molecules include enzymes, radiolabels, haptens, fluorescent labels, phosphorescent molecules, chemiluminescent molecules, chromophores, photoaffinity molecules, colored particles or ligands, such as biotin. The labels used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^3$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies may be produced according to well-known methods in the art.

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

IV. DETECTION METHODS

In one aspect, the disclosure provides method for detection and quantitation of FALD-GSH, and the diagnosis of eosinophilic abnormalities based thereon. A variety of different methodologies are available for the detection of FALD-GSH. In general, one can detect either FALD-GSH using antibodies that bind specifically or preferentially to this molecule, or one can employ HPLC and/or mass spectrometric methods. These technologies are described in greater detail below.

A. Mass Spectrometry

By exploiting the intrinsic properties of mass and charge, mass spectrometry (MS) can resolved and confidently identified a wide variety of complex compounds, including proteins. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). In accordance with the present invention, one can generate mass spectrometry profiles that are useful for grading gliomas and predicting glioma patient survival, without regard for the identity of specific proteins. Alternatively, given the established links with calcyclin, calpactin I light chain, astrocytic phosphoprotein PEA-15 and tubulin-specific chaperone A, mass spectrometry may be used to look for the levels of these proteins particularly.

1. ESI

ESI is a convenient ionization technique developed by Fenn and colleagues (Fenn et al., 1989) that is used to produce gaseous ions from highly polar, mostly nonvolatile biomolecules, including lipids. The sample is injected as a liquid at low flow rates (1-10 µl/min) through a capillary tube to which a strong electric field is applied. The field generates additional charges to the liquid at the end of the capillary and produces a fine spray of highly charged droplets that are electrostatically attracted to the mass spectrometer inlet. The evaporation of the solvent from the surface of a droplet as it travels through the desolvation chamber increases its charge density substantially. When this increase exceeds the Rayleigh stability limit, ions are ejected and ready for MS analysis.

A typical conventional ESI source consists of a metal capillary of typically 0.1-0.3 mm in diameter, with a tip held approximately 0.5 to 5 cm (but more usually 1 to 3 cm) away from an electrically grounded circular interface having at its center the sampling orifice, such as described by Kabarle et al. (1993). A potential difference of between 1 to 5 kV (but more typically 2 to 3 kV) is applied to the capillary by power supply to generate a high electrostatic field ($10^6$ to $10^7$ V/m) at the capillary tip. A sample liquid carrying the analyte to be analyzed by the mass spectrometer, is delivered to tip through an internal passage from a suitable source (such as from a chromatograph or directly from a sample solution via a liquid flow controller). By applying pressure to the sample in the capillary, the liquid leaves the capillary tip as small highly electrically charged droplets and further undergoes desolvation and breakdown to form single or multicharged gas phase ions in the form of an ion beam. The ions are then collected by the grounded (or negatively charged) interface plate and led through an the orifice into an analyzer of the mass spectrometer. During this operation, the voltage applied to the capillary is held constant. Aspects of construction of ESI sources are described, for example, in U.S. Pat. Nos. 5,838,002; 5,788,166; 5,757,994; RE 35,413; and U.S. Pat. No. 5,986,258.

2. ESI/MS/MS

In ESI tandem mass spectroscopy (ESI/MS/MS), one is able to simultaneously analyze both precursor ions and product ions, thereby monitoring a single precursor product reaction and producing (through selective reaction monitoring (SRM)) a signal only when the desired precursor ion is present. When the internal standard is a stable isotope-labeled version of the analyte, this is known as quantification by the stable isotope dilution method. This approach has been used to accurately measure pharmaceuticals (Zweigenbaum et al., 2000; Zweigenbaum et al., 1999) and bioactive peptides (Desiderio et al., 1996; Lovelace et al., 1991).

Newer methods are performed on widely available MALDI-TOF instruments, which can resolve a wider mass range and have been used to quantify metabolites, peptides, and proteins. Larger molecules such as peptides can be quantified using unlabeled homologous peptides as long as their chemistry is similar to the analyte peptide (Duncan et al., 1993; Bucknall et al., 2002). Protein quantification has been achieved by quantifying tryptic peptides (Mirgorodskaya et al., 2000). Complex mixtures such as crude extracts can be analyzed, but in some instances sample clean up is required (Nelson et al., 1994; Gobom et al., 2000).

3. SIMS

Secondary ion mass spectroscopy, or SIMS, is an analytical method that uses ionized particles emitted from a surface for mass spectroscopy at a sensitivity of detection of a few parts per billion. The sample, surface is bombarded by primary energetic particles, such as electrons, ions (e.g., O, Cs), neutrals or even photons, forcing atomic and molecular particles to be ejected from the surface, a process called sputtering. Since some of these sputtered particles carry a charge, a mass spectrometer can be used to measure their mass and charge. Continued sputtering permits measuring of the exposed elements as material is removed. This in turn permits one to construct elemental depth profiles. Although the majority of secondary ionized particles are electrons, it is the secondary ions which are detected and analysis by the mass spectrometer in this method.

4. LD-MS and LDLPMS

Laser desorption mass spectroscopy (LD-MS) involves the use of a pulsed laser, which induces desorption of sample material from a sample site—effectively, this means vaporization of sample off of the sample substrate. This method is usually only used in conjunction with a mass spectrometer, and can be performed simultaneously with ionization if one uses the right laser radiation wavelength.

When coupled with Time-of-Flight (TOF) measurement, LD-MS is referred to as LDLPMS (Laser Desorption Laser Photoionization Mass Spectroscopy). The LDLPMS method of analysis gives instantaneous volatilization of the sample, and this form of sample fragmentation permits rapid analysis without any wet extraction chemistry. The LDLPMS instrumentation provides a profile of the species present while the retention time is low and the sample size is small. In LDLPMS, an impactor strip is loaded into a vacuum chamber. The pulsed laser is fired upon a certain spot of the sample site, and species present are desorbed and ionized by the laser radiation. This ionization also causes the molecules to break up into smaller fragment-ions. The positive or negative ions made are then accelerated into the flight tube, being detected at the end by a microchannel plate detector. Signal intensity, or peak height, is measured as a function of travel time. The applied voltage and charge of the particular ion determines the kinetic energy, with separation of fragments due to different size causing different velocity. Each ion mass will thus have a different flight-time to the detector.

One can either form positive ions or negative ions for analysis. Positive ions are made from regular direct photoionization, but negative ion formation requires a higher powered laser and a secondary process to gain electrons. Most of the molecules that come off the sample site are neutrals, and thus can attract electrons based on their electron affinity. The negative ion formation process is less efficient than forming just positive ions. The sample constituents will also affect the outlook of a negative ion spectra.

Other advantages with the LDLPMS method include the possibility of constructing the system to give a quiet baseline of the spectra because one can prevent coevolved neutrals from entering the flight tube by operating the instrument in a linear mode. Also, in environmental analysis, the salts in the air and as deposits will not interfere with the laser desorption and ionization. This instrumentation also is very sensitive, known to detect trace levels in natural samples without any prior extraction preparations.

5. MALDI-TOF-MS

Since its inception and commercial availability, the versatility of MALDI-TOF-MS has been demonstrated convincingly by its extensive use for qualitative analysis. For example, MALDI-TOF-MS has been employed for the characterization of synthetic polymers (Marie et al., 2000; Wu et al., 1998). peptide and protein analysis (Roepstorff et al., 2000; Nguyen et al., 1995), DNA and oligonucleotide sequencing (Miketova et al., 1997; Faulstich et al., 1997; Bentzley et al., 1996), and the characterization of recombinant proteins (Kanazawa et al., 1999; Villanueva et al., 1999). Recently, applications of MALDI-TOF-MS have been extended to include the direct analysis of biological tissues and single cell organisms with the aim of characterizing endogenous peptide and protein constituents (Li et al., 2000; Lynn et al., 1999; Stoeckli et al., 2001; Caprioli et al., 1997; Chaurand et al., 1999; Jespersen et al., 1999).

The properties that make MALDI-TOF-MS a popular qualitative tool—its ability to analyze molecules across an extensive mass range, high sensitivity, minimal sample preparation and rapid analysis times—also make it a potentially useful quantitative tool. MALDI-TOF-MS also enables non-volatile and thermally labile molecules to be analyzed with relative ease. It is therefore prudent to explore the potential of MALDI-TOF-MS for quantitative analysis in clinical settings, for toxicological screenings, as well as for environmental analysis. In addition, the application of MALDI-TOF-MS to the quantification of peptides and proteins is particularly relevant. The ability to quantify intact proteins in biological tissue and fluids presents a particular challenge in the expanding area of proteomics and investigators urgently require methods to accurately measure the absolute quantity of proteins. While there have been reports of quantitative MALDI-TOF-MS applications, there are many problems inherent to the MALDI ionization process that have restricted its widespread use (Kazmaier et al., 1998; Horak et al., 2001; Gobom et al., 2000; Wang et al., 2000; Desiderio et al., 2000). These limitations primarily stem from factors such as the sample/matrix heterogeneity, which are believed to contribute to the large variability in observed signal intensities for analytes, the limited dynamic range due to detector saturation, and difficulties associated with coupling MALDI-TOF-MS to on-line separation techniques such as liquid chromatography. Combined, these factors are thought to compromise the accuracy, precision, and utility with which quantitative determinations can be made.

Because of these difficulties, practical examples of quantitative applications of MALDI-TOF-MS have been limited. Most of the studies to date have focused on the quantification of low mass analytes, in particular, alkaloids or active ingredients in agricultural or food products (Wang et al., 1999; Jiang et al., 2000; Wang et al., 2000; Yang et al., 2000; Wittmann et al., 2001), whereas other studies have demonstrated the potential of MALDI-TOF-MS for the quantification of biologically relevant analytes such as neuropeptides, proteins, antibiotics, or various metabolites in biological tissue or fluid (Muddiman et al., 1996; Nelson et al., 1994; Duncan et al., 1993; Gobom et al., 2000; Wu et al., 1997; Mirgorodskaya et al., 2000). In earlier work it was shown that linear calibration curves could be generated by MALDI-TOF-MS provided that an appropriate internal standard was employed (Duncan et al., 1993). This standard can "correct" for both sample-to-sample and shot-to-shot variability. Stable isotope labeled internal standards (isotopomers) give the best result.

With the marked improvement in resolution available on modern commercial instruments, primarily because of delayed extraction (Bahr et al., 1997; Takach et al., 1997), the opportunity to extend quantitative work to other examples is now possible; not only of low mass analytes, but also biopolymers. Of particular interest is the prospect of absolute multi-component quantification in biological samples (e.g., proteomics applications).

The properties of the matrix material used in the MALDI method are critical. Only a select group of compounds is useful for the selective desorption of proteins and polypeptides. A review of all the matrix materials available for peptides and proteins shows that there are certain characteristics the compounds must share to be analytically useful. Despite its importance, very little is known about what makes a matrix material "successful" for MALDI. The few materials that do work well are used heavily by all MALDI practitioners and new molecules are constantly being evaluated as potential matrix candidates. With a few exceptions, most of the matrix materials used are solid organic acids. Liquid matrices have also been investigated, but are not used routinely.

B. High Performance Liquid Chromatography

High-performance liquid chromatography (HPLC; formerly referred to as high-pressure liquid chromatography), is a technique in analytic chemistry used to separate the components in a mixture, to identify each component, and to quantify each component. It relies on pumps to pass a pressurized liquid solvent containing the sample mixture through a column filled with a solid adsorbent material. Each component in the sample interacts slightly differently with the adsorbent material, causing different flow rates for the different components and leading to the separation of the components as they flow out the column.

HPLC has been used for medical (e.g., detecting vitamin D levels in blood serum), legal (e.g., detecting performance enhancement drugs in urine), research (e.g., separating components of a complex biological sample, or of similar synthetic chemicals from each other), and manufacturing (e.g., during the production process of pharmaceutical and biological products) purposes.

Chromatography can be described as a mass transfer process involving adsorption. HPLC relies on pumps to pass a pressurized liquid and a sample mixture through a column filled with a sorbent, leading to the separation of the sample components. The active component of the column, the sorbent, is typically a granular material made of solid particles (e.g., silica, polymers, etc.), 2-50 micrometers in size. The components of the sample mixture are separated from each other due to their different degrees of interaction with the sorbent particles. The pressurized liquid is typically a mixture of solvents (e.g., water, acetonitrile and/or methanol) and is referred to as a "mobile phase." Its composition and temperature play a major role in the separation process by influencing the interactions taking place between sample components and sorbent. These interactions are physical in nature, such as hydrophobic (dispersive), dipole-dipole and ionic, most often a combination thereof.

HPLC is distinguished from traditional ("low pressure") liquid chromatography because operational pressures are significantly higher (50-350 bar), while ordinary liquid chromatography typically relies on the force of gravity to pass the mobile phase through the column. Due to the small sample amount separated in analytical HPLC, typical column dimensions are 2.1-4.6 mm diameter, and 30-250 mm length. Also HPLC columns are made with smaller sorbent particles (2-50 micrometer in average particle size). This gives HPLC superior resolving power when separating mixtures, which is why it is a popular chromatographic technique.

An HPLC instrument typically includes a sampler, pumps, and a detector. The sampler brings the sample mixture into the mobile phase stream which carries it into the column. The pumps deliver the desired flow and composition of the mobile phase through the column. The detector generates a signal proportional to the amount of sample component emerging from the column, hence allowing for quantitative analysis of the sample components. A digital microprocessor and user software control the HPLC instrument and provide data analysis. Some models of mechanical pumps in a HPLC instrument can mix multiple solvents together in ratios changing in time, generating a composition gradient in the mobile phase. Various detectors are in common use, such as UV/Vis, photodiode array (PDA) or based on mass spectrometry. Most HPLC instruments also have a column oven that allows for adjusting the temperature the separation is performed at.

C. Immunodetection

In further embodiments, there are immunodetection methods for identifying and/or quantifying FALD-GSH. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev (1999), Gulbis and Galand 0993), De Jager et al. (1993), and Nakamura et al. (1987). In general, the immunobinding methods include obtaining a sample and contacting the sample with a first antibody in accordance with embodiments discussed herein, as the case may be, under conditions effective to allow the formation of immunocomplexes. It is also possible to perform in vivo assays.

Contacting the chosen biological sample with an antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to foci-related proteins. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

1. ELISAs

Immunoassays are, in their most simple and direct sense, binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a test composition suspected of containing the foci is added to the wells. After binding and washing to remove non-specifically bound immune complexes, the bound antigen may be detected. Detection may be achieved by the addition of another anti-foci antibody that is linked to a detectable label. This type of ELISA is a simple "sandwich ELISA." Detection may also be achieved by the addition of a second anti-foci antibody, followed by the addition of a third antibody that has binding affinity for the second antibody, with the third antibody being linked to a detectable label.

In another exemplary ELISA, the samples suspected of containing the foci are immobilized onto the well surface and then contacted with anti-foci antibody. After binding and washing to remove non-specifically bound immune complexes, the bound anti-foci antibodies are detected. Where the initial anti-foci antibodies are linked to a detectable label, the immune complexes may be detected directly. Again, the immune complexes may be detected using a second antibody that has binding affinity for the first anti-foci antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

2. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their nonspecific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

3. Immunohistochemistry

The antibodies may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1999; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

V. THERAPIES

When patients are diagnosed as having any of the aforemetioned diseases using methods described herein, medical management of these diseases may be undertaken. Such treatments are mentioned elsewhere in this document, and that discussion is incorporated by reference here.

VI. KITS

Any of the compositions described herein may be comprised in a kit. In a non-limiting example, an antibody targeting FALD-GSH may be included in a kit. The kit may further include a sterile buffer to facilitate dilution. The antibody may be labeled, such as with a fluorescent label.

The kits will thus comprise, in suitable container means, a first antibody that binds to FALD-GSH, and optionally an immunodetection reagent. The antibody may be pre-bound to a solid support, such as a column matrix and/or well of a microtitre plate. The antibodies may have detectable labels that are associated with or linked to the given antibody. Detectable labels that are associated with or attached to a secondary binding ligand are also contemplated. Exemplary secondary ligands are those secondary antibodies that have binding affinity for the first antibody.

The kits may further comprise a suitably aliquoted composition of FALD-GSH, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present disclosure also will typically include a means for containing the antibodies and any other reagent containers in close confinement for commercial sale. Such containers may include injection or blow-molded plastic containers into which the desired vials are retained. Instructions may include variations that can be implemented.

When the components of the kit are provided in one and/or more liquid solutions, the liquid solution is an aqueous solution, with a sterile aqueous solution being particularly preferred. However, the active agent may be provided as dried powder(s). When reagents and/or components are provided as a dry powder, the powder can be reconstituted by the addition of a suitable solvent. It is envisioned that the solvent may also be provided in another container means. Such kits may also include components that preserve or maintain the active agent that protect against its degradation.

VII. EXAMPLES

The following examples are included to demonstrate certain non-limiting aspects of the disclosure. It should be appreciated by those of skill in the art that the techniques disclosed in the following examples represent techniques discovered by the inventor to function well in the practice of the disclosure. However, those of skill in the art should, in light of the present disclosure, appreciate that many changes can be made in the specific embodiments which are disclosed and still obtain a like or similar result without departing from the spirit and scope of the disclosure.

Example 1

Materials & Methods

Reagents. HPLC grade methanol, acetonitrile, and isopropanol were purchased from Fisher Scientific. TLC Plates (20×20 cm, 40 Å silica gel) were obtained from EMB Millipore. [7,7,8,8-d4]hexadecanoic acid was purchased from Medical Isotopes. All other chemicals were purchased from Sigma-Aldrich or Fisher Scientific.

Instrumentation. Mass spectrometry was performed using a Thermo Fisher TSQ Quantum Ultra mass spectrometer (Thermo Fisher, Waltham, Mass., USA). For experiments requiring LC-MS, a Thermo Fisher Surveyor MS LC system was coupled to the same mass spectrometer using the indicated column (vide infra). LC-MS data analysis was performed using XCalibur software (Thermo Fisher).

Methods. TLC Resolution 2-Chlorohexadecanal and Glutathione in vitro Reaction products: All reactions were carried out in PBS (pH 7.4), methanol, and ethyl ether at a ratio of 0.6:1.5:2. Briefly, 2-ClHDA or HDA were first suspended in 73 uL of ethyl ether in a clean, borosilicate reaction vessel. 55 µl MEOH was then added±n-ethylmaleimide (NEM). Finally, GSH was added in 22 µl PBS and the reaction mixture was vortexed and allowed to react in a sealed reaction vessel at 37° C. for 4 hours. Reaction solutions (10 µl) were loaded onto 40 Å silica gel TLC plates. Chromatographic separation was attained with a $CHCl_3$/acetone/MEOH/$H_2O$/acetic acid (6/8/2/2/1 v/v/v/v/v) mobile phase. TLC plates where visualized with the amine stain, ninhydrin or 2,4-dinitrophenylhydrazine (DNPH) to stain aldehydes. TLC lanes used for purification were not stained but scrapped and extracted using 1 mL of ACN/$H_2O$ (7/3 v/v) with 0.25% formic acid. The solution was centrifuged at 2,000 g for 5 minutes and the supernatant removed. The supernatant was dried under a stream of N2 and suspend in 150 µl ACN/$H_2O$ (7:3 v/v) with 0.1% formic acid. The suspension was then used for ESI-MS/MS analysis and further TLC visualization.

Electrospray Mass Spectrometry Characterization: TLC purified HDA-GSH was diluted 2000× with ACN/$H_2O$ (7:3) with 0.1% formic acid and directly injected onto the Thermo Fisher TSQ Quantum Ultra mass spectrometer at a flow rate of 5 µl/min. For electrospray ionization MS (Q1), the ionization energy and temperature were 3700V and 270° C. respectively for positive ion mode and 2600V and 270° C. for negative ion mode. Further structural data was gathered through Q2 fragmentation with a collision energy of 15 eV and collision gas of 1.0 Torr argon for both the positive and negative ions and analysis of the Q3 fragments.

Deuterated HDA-GSH Synthesis: Commercially available [7,7,8,8-$d_4$]-hexadecanoic acid was converted to 2-bromohexadecanal (2-BrHDA) as previously described (2). 150 mg 2-BrHDA was then reacted with 300 mg GSH in 3 ml of 2/1.5/0.6 (Ethyl Ether/MEOH/$H_2O$ v/v/v) for 4 hr at 37° C. The single phase reaction solution was then broken with 10 ml $H_2O$ and 15 mL ethyl ether. The ethyl ether layer including interface was extracted and dried to a white solid. The white solid was sequentially washed with 3×10 ml Hexane, 2×10 ml MEOH, and 2×10 ml $H_2O$ to remove any remaining free 2-BrHDA and GSH. The final product was brought to dryness by lyophilization and weighed. The resulting product was analyzed by direction injection ESI-MS/MS and found to be pure [$d_4$]-HDA-GSH.

RAW 264.7 Cell 2-ClHDA Treatments: RAW 264.7 cells were treated with Dubelco's Modified Eagle's Medium (DMEM) supplemented with 2% Fetal Bovine Serum (FBS) and 0, 1, 5, 25, or 50 μM 2-ClHDA for 8 hours. The media was then removed and cells washed with PBS. The cells were scraped in 1.25 ml PBS containing 10 mM N-ethylmaleimide (NEM) and immediately frozen. 10 mM NEM was added to the final cell homogenate solution to block any free GSH sulfhydryls from spontaneously reacting with α-chlorofatty aldehydes (α-ClFAlD) in following extraction procedures although no spontaneous production has been observed.

PMA stimulated Neutrophils: Primary human neutrophils were isolated as previously published (1). Briefly, enriched neutrophils were diluted to 1 million neutrophils per ml in Hanks buffer solution. 200 nM phorbol-12-myristate 13-acetate (PMA) in EtOH (0.1%) and 10 mM aminotriazole were then added to respective experiments. The solutions were allowed to incubate for 30 min at 37° C. At the end of each reaction, 10 mM NEM was added and the neutrophils were immediately frozen.

Extraction and Quantification of (α-ClFAlD) conjugates of GSH: To extract and quantitate 2-ClHDA conjugates of GSH, 90 fmols of [$d_4$]-HDA-GSH and 1 volume of MEOH/ACN (1/1 v/v) were added to 100 μl of the Raw cell homogenate, and 45 fmols of [$d_4$]-HDA-GSH and 1 volume of MEOH/ACN (1/1 v/v) were added to 1 ml neutrophil homogenate. The solutions were then vortexed and briefly sonicated. The resulting solution was centrifuged at 1,000 g for 5 min, and the supernatant removed. The supernatant was loaded on a Strata-X (60 mg bed weight) conditioned with 1.2 ml MEOH followed by 1.2 ml $H_2O$/MEOH (4/1 v/v). Following the load, the column was washed with 2×0.6 ml $H_2O$/MEOH (4/1 v/v). 2-ClHDA conjugates of GSH were eluted with 2×0.6 ml of MEOH/ACN (3/1 v/v) with 0.25% formic acid. The eluate was dried under N2 and suspended in 100 μl 6:4:5 ACN:IPA:$H_2O$ (0.15% formic acid) for analysis by LC-MS/MS.

A Phenomenex Onyx Monolithic (50×2.0 mm) column was coupled to the ESI-MS/MS to allow for precise quantitation of the GSH adducts using single reaction monitoring (SRMs). Solvent A was ACN/IPA (3/2 v/v) with 0.25% formic acid and B was $H_2O$ (0.25% formic acid). The column was equilibrated with 65/35 A/B followed by the injection 25 μl of the Strata-X purified solutions onto the column. GSH adducts of 2-ClHDA were eluted by a 2.5 min gradient of 35 to 100% B.

Example 2

Results

2-Chlorohexadecanal Forms in vitro Adducts with Glutathione. The alpha carbon of 2-chlorohexadecanal (2-ClHDA) bound by chlorine may be a target for modification by cellular nucleophiles. Scheme 1 demonstrates the structure of 2-ClHDA and its electrophilic target carbons that were theorized to be available for modification.

SCHEME 1

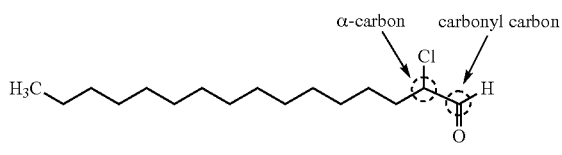

Glutathione (GSH) is a ubiquitous cellular nucleophile that is known to bind electrophilic lipids and is a likely candidate for cellular modification of α-ClFAlD.

The α-ClFAlD, 2-ClHDA, and GSH were reacted at a 2:1 molar excess of 2-ClHDA in a test tube for four hours. FIGS. 1A-B demonstrate that a new, more lipophilic compound that runs faster on a TLC plate (Rf≈2.4) than GSH (Rf≈0.9) is resolved by silica TLC chromatography (lane 3) with a polar lipid solvent system. The new compound is stained by Ninhydrin (FIG. 1A), which readily stains the amine of GSH, but does not stain 2-ClHDA. Additionally, the new compound is also stained by DNPH (FIG. 1B), which stains aldehydes such as 2-ClHDA and hexadecanal (HDA) that can be seen at the solvent front, but does not stain GSH. As the new compound stains for both amines and aldehydes, it is likely a GSH conjugate of 2-ClHDA.

When HDA, which contains no chlorine at the alpha position, is reacted with GSH, no new product is formed (FIGS. A-B, lane 5). This implicates the alpha position chlorine as essential to the adduction mechanism. When N-ethylmaleimide (NEM) was added to the reaction solution just prior to GSH, 2-ClHDA did not form an adduct with GSH. As NEM readily binds the sulfhydryl of GSH (FIGS. 1A-B, lane 6), GSH is likely binding 2-ClHDA through a thiol-related mechanism.

Characterization of HDA-GSH Adduct by Mass Spectrometry. To directly characterize the 2-ClHDA-GSH adduct observed by TLC, the novel band (Rf≈2.4) was extracted off the TLC plate. FIG. 2A demonstrates that pure 2-ClHDA-GSH adduct was attained by extraction (lane 2). The TLC purified band was then diluted and analyzed by direct injection on a Thermo Fisher TSQ Quantum Ultra mass spectrometer. In positive ion survey mode, the predominating [M+H]$^+$ ion was 546.36 (FIG. 2B). The proposed structure for this compound (FIG. 2D) based on a molecular weight of 545.36 has the GSH thiol substituting the chlorine at the alpha position of 2-ClHDA to form a dechlorinated HDA-GSH adduct. Additional ions found in the positive scan correlate with the common addition of Na (+22, 568.32) and loss of $H_2O$ (−18, 528.30). The fourth ion found in the positive ion survey scan, 399.30, is a common fragment of GSH adducts of lipids that corresponds to the loss of pyroglutamate and $H_2O$ from the parent ion, 546.36.

Figure 3A:
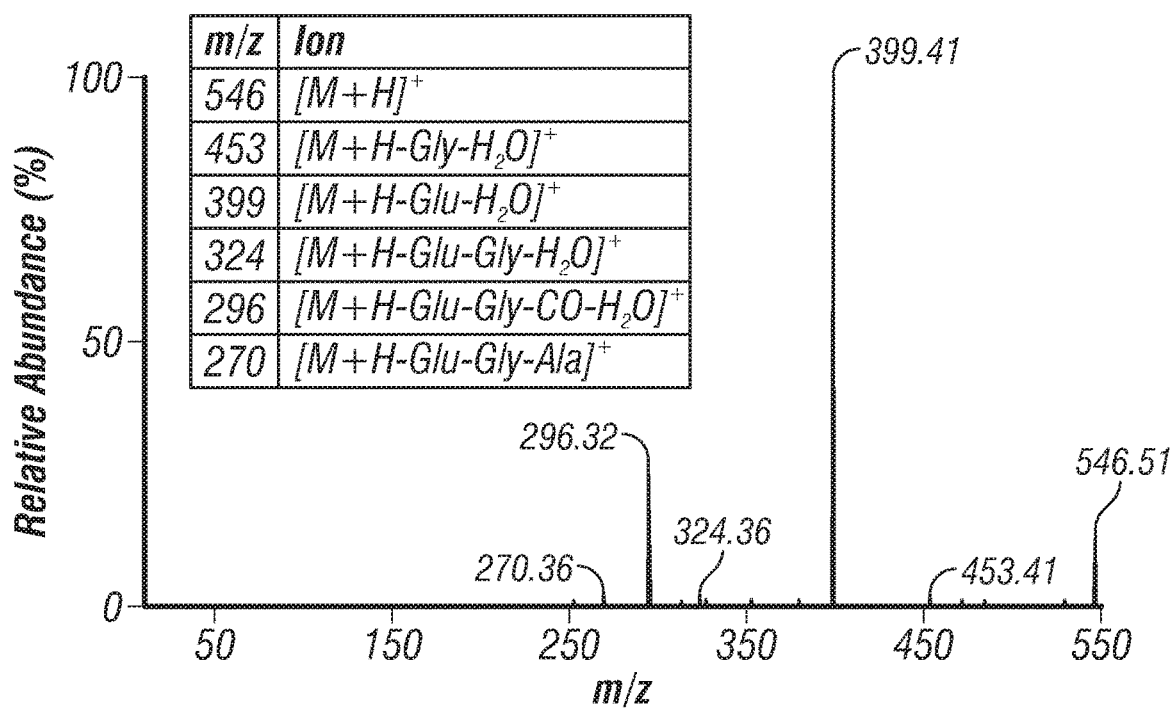
FIGS. 3A-B. ESI-MS/MS of HDA-GSH. TLC-purified HDA-GSH was analyzed by direct infusion ESI and subjected to MS/MS analysis at 15 eV and 1.0 Torr. MS/MS spectra for the $[M+H]^+$ parent ion at m/z 546.36 (FIG. 3A) and the $[M-H]^-$ parent ion at m/z 544.66 (FIG. 3B) are shown. Inset tables provide likely fragment ion assignments.
Figure 3B:
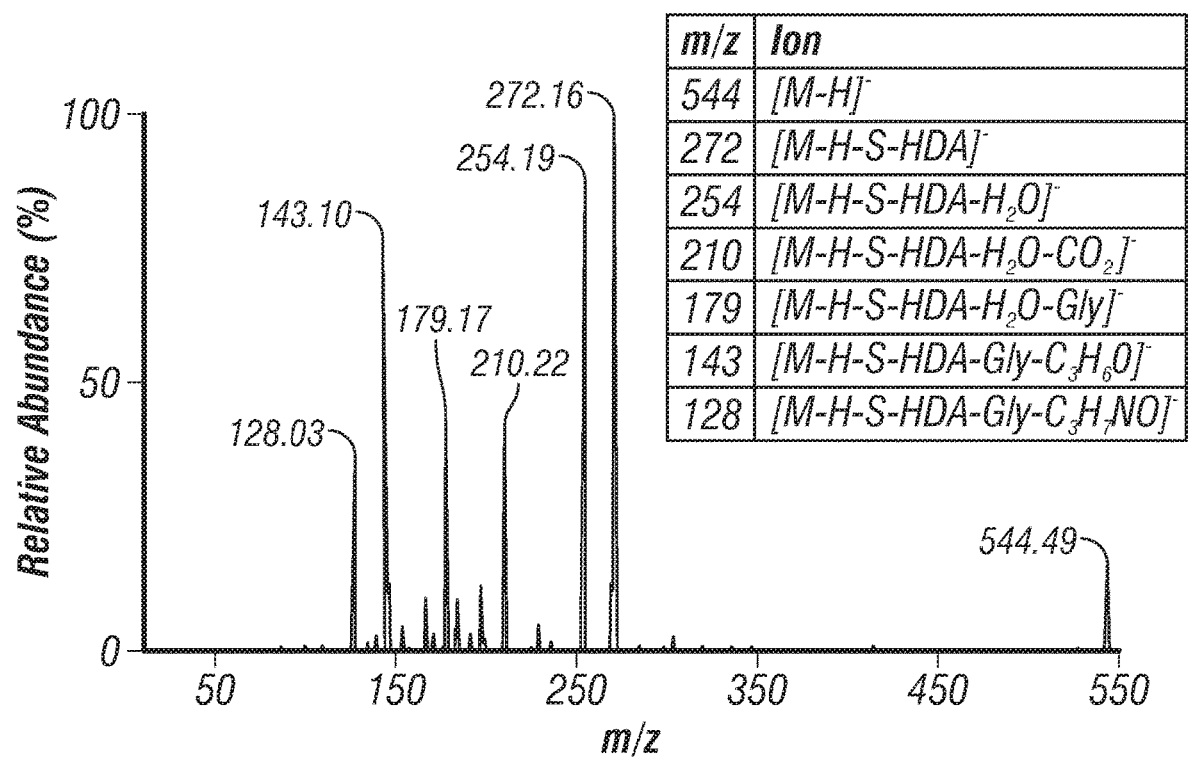

FIG. 2C displays the negative ion survey scan of the TLC purified HDA-GSH, which complements the positive ion scan. The prevailing ion is the [M−H]$^-$, 544.66, which supports the proposed HDA-GSH structure. The second ion, 566.22, again is a common addition of Na (+22, 566.66). To further characterize the HDA-GSH adduct, both the [M+H]$^+$ and [M−H]$^-$ ions were subjected to MS/MS fragmentation and analysis. The positive parent ion, 546.36 [M+H]$^+$, fragments into two major ions, 399.41 and 296.2 (FIG. 3A). The 399.41 fragment corresponds with the loss of pyroglutamate and $H_2O$ as previously stated and the 296.32 ion also losses the glycine moiety of GSH and the carbonyl of cysteine in addition to the loss of pyroglutamate and $H_2O$. Additional experiments examined the reactivity of cysteine with 2-ClHDA and revealed a readily formed adduct with 296.32 as the primary ion formed (data not shown). The negative parent ion, 544.66 [M+H]$^+$, fragments into multiple ions (FIG. 3B) that directly correspond to the known fragmentation of GSH. The predominating ion, 272.16 is the cleavage of HDA-GSH at sulfhydryl as demonstrated in the FIG. 3B inset. Both the positive and negative ion survey scan and parent ion fragmentations support the structure proposed in FIG. 2D.

To verify that the aldehyde remains free after the formation of HDA-GSH from glutathione and 2-ClHDA, HDA-GSH was reacted with 2,4-Dinitrophenylhydrazine (DNPH) to solely modify the aldehyde. FIG. 4A shows the expected [M+H]$^+$ shift from 546.29 to the DNPH derivative at 726.19. FIG. 4B displays the fragmentation pattern of the DNPH derivative displayed in FIG. 4C. The DNPH derivative verifies the HDA-GSH stricture containing a free aldehyde proposed in FIG. 2.

Figure 5:
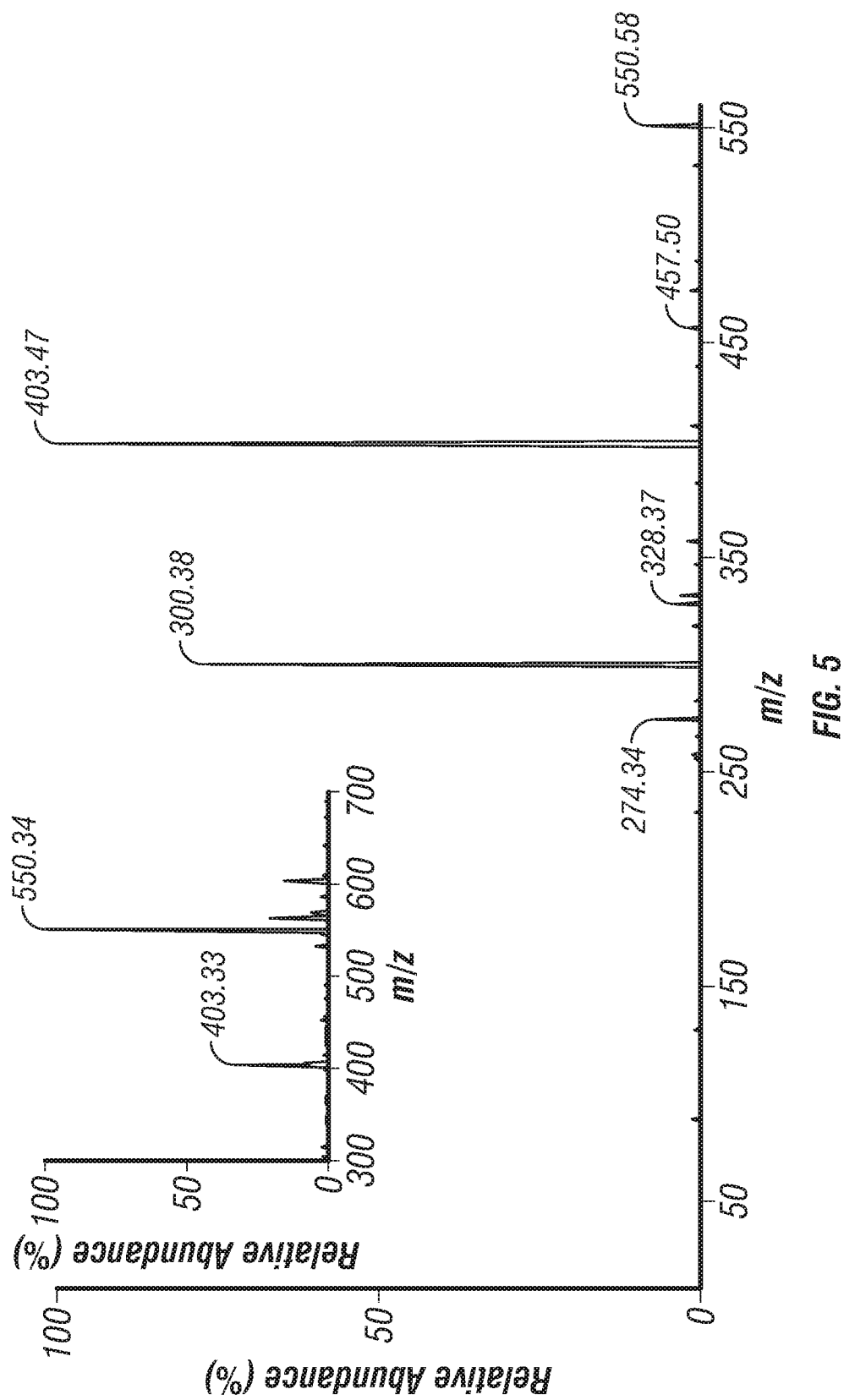
FIG. 5. ESI-MS and MS/MS analysis of $[d_4]$-HDA-GSH. Synthetic $[d_4]$-HDA-GSH was analyzed by direct infusion in the positive ion mode with MS/MS analyses as described in FIGS. 3A-B. MS/MS analysis of the $[M+H]^+$ ion at m/z 550.35 displays a distinct 4 amu shift compared to the HDA-GSH fragment ions. Survey mode positive ions of synthetic $[d_4]$-HDA-GSH are shown in the spectra of the inset.

Characterization of [d$_4$]-HDA-GSH. To quantitatively determine whether α-ClFALD produced in primary cells are able to adduct GSH, the deuterated equivalent to HDA-GSH, [d$_4$]-HDA-GSH, was synthesized. The purified [d$_4$]-HDA-GSH was weighed and its purity and structure were verified by direct ESI-MS/MS analysis. FIG. 5 demonstrates that the deuterated product [M+H]$^+$ is shifted 4 m/z from the natural product to 550.34 as would be expected. The positive ion fragments that retain the fatty aldehyde moiety also show a 4 m/z shift, which also supports the original structure proposed in FIG. 2D.

Figure 6:
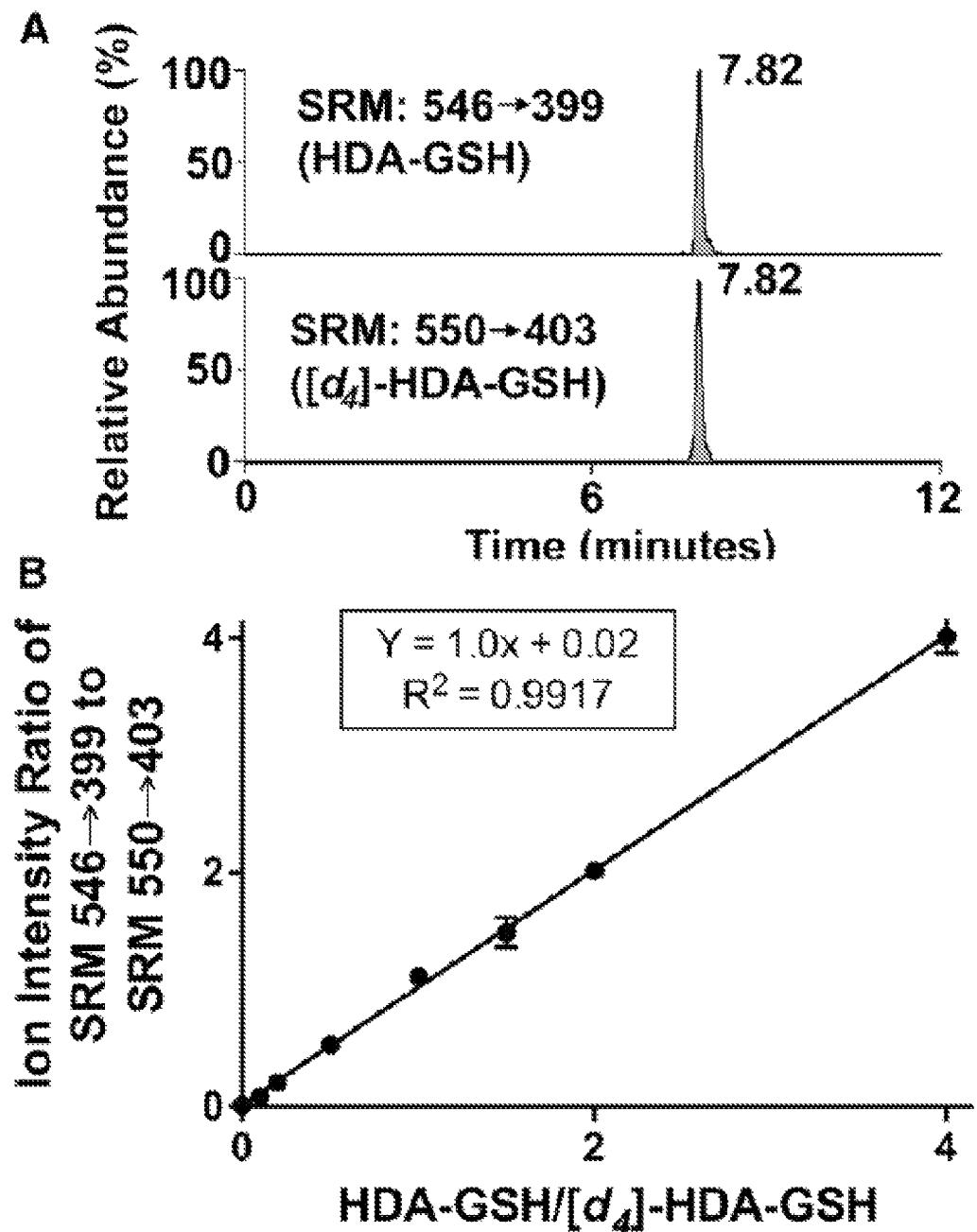
FIGS. 6A-B. Stable isotope dilution quantitation of HDA-GSH by LC-ESI-MS/MS. Based on the fragmentation ions shown in FIGS. 3A-B and 4A-C, LC-MS with SRM detection was used to quantify HDA-GSH. Using LC-MS, 15 fmol HDA-GSH and 15 fmol $[d_4]$-HDA-GSH were detected in the SRM scan mode, SRM 546→399 and m/z 550→403, respectively (as indicated in FIG. 6A). In triplicate, selected amounts of HDA-GSH in the presence of a fixed amount of $[d_4]$-HDA-GSH (7 fmol) were extracted in and then were subjected to LC-MS/MS. The peak area ratios were plotted versus the ratio of the HDA-GSH and $[d_4]$-HDA-GSH injected yielding a response line (FIG. 6B).

Quantitation of HDA-GSH by LCMS/MS. Utilizing purified natural HDAGSH and [d$_4$]-HDA-GSH, a rapid, repeatable, and quantifiable LC-MS/MS technique was developed. Utilizing the fragmentation information already gathered, selective reaction monitoring (SRM) was used to accurately and sensitively detect both the natural and deuterated HDA-GSH compounds. The SRM of 546.34→399.41 was used for natural HDA-GSH and 550.34→403.41 for [d$_4$]-HDA-GSH. Additionally using this method ODA-GSH is detected by the SRM 574.34→427.41. FIG. 6A shows a chromatogram using the elution gradient described in "Material and Methods" with an elution time of the natural and deuterated HDA-GSH elute at the same time (Rt 7.82 min).

To confirm that ionization and fragmentation patterns of the deuterated product were comparable to the natural product, natural HDAGSH levels were varied while maintaining a constant [d$_4$]-HDA-GSH levels. The resulting plot (FIG. 6B) demonstrates that the slope is 1 and that [d$_4$]-HDA-GSH is an excellent internal standard for natural HDA-GSH with a response factor of unity. Using the method described here, the inventors were able to repeatedly and quantifiably detect HDA-GSH levels as low as 5 fmol.

Figure 7:
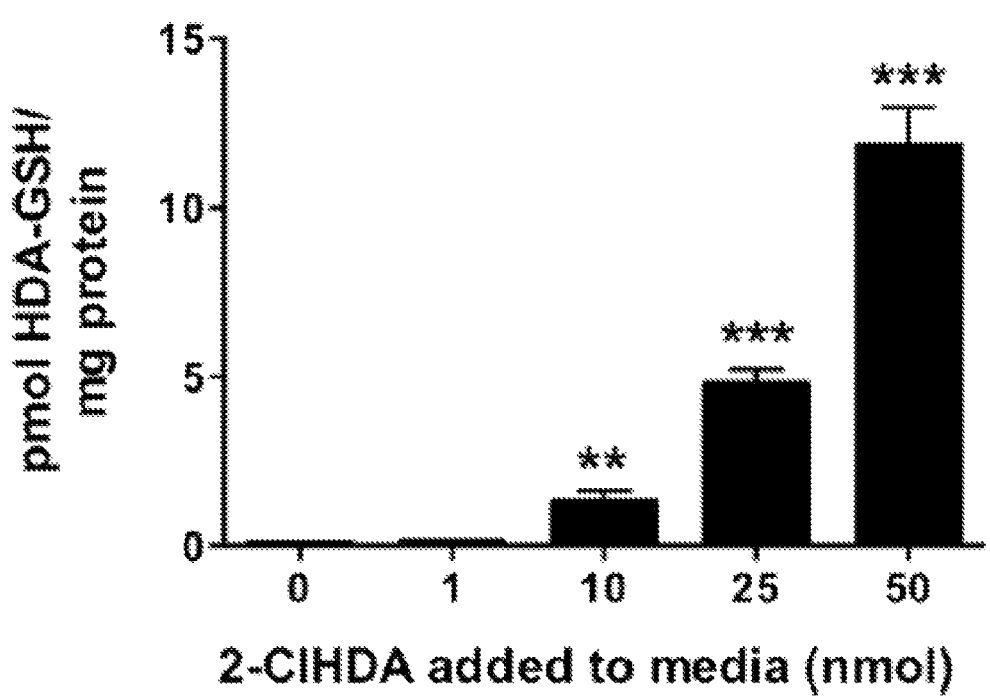
FIG. 7. Quantitation of HDA-GSH production in RAW 264.7 cells treated with 2-ClHDA. RAW 264.7 cells were treated with indicated concentrations of 2-ClHDA for 8 hr. HDA-GSH produced was quantified using the added $[d_4]$-HDA-GSH as internal standard following LC-ESI-MS/MS with SRM detection.  and * indicate $p<0.01$ and $0.001$, respectively, for comparisons to no 2-ClHDA added to media. n=3 for each treatment.

Production of HDA-GSH in RAW 264.7 Cells Treated with 2-ClHDA. To determine whether cells are capable of producing HDA-GSH in the presence of physiological levels of 2-ClHDA, RAW 264.7 mouse macrophages were treated with 2-ClHDA for 8 hours and then analyzed for HDA-GSH production. α-ClFALD production is the direct result of myeloperoxidase (MPO) activity in monocytes, macrophages, and neutrophils and therefore, α-ClFAlD adducts of GSH are likely found in the same cells. RAW 264.7 cells were chosen as they are a well characterized macrophage system, but incapable of producing 2-ClHDA. All HDA-GSH produced in RAW 264.7 cells can be directly attributed to the exogenous 2-ClHDA. To enhance sensitivity and reproducibility of detection, HDA-GSH was first purified out of the cell homogenate using Strata-X columns as described in the methods. No HDA-GSH was detected in the EtOH controls while HDA-GSH levels were elevated in a concentration dependent manor between 10-50 μM 2-ClHDA treatments (FIG. 7).

HDA-GSH and ODA-GSH Accumulation in PMA Stimulated Neutrophils. Isolated primary human neutrophils stimulated with phorbal myristic acid (PMA) readily produce α-ClFAlD (1) and were therefore assayed for the production of α-ClFALD adducts of GSH. FIG. 8A shows a time course of α-ClFAlD production in 200 nM PMA stimulated neutrophils. Both the 16-carbon 2-chlorohexadecanal (2-ClHDA) and 18-carbon 2-chlorooctadecanal (2-ClODA) α-ClFAlD molecular species were elevated by 5 min, peak by 30 min and begin to decline by 60 min.

Interestingly, the production of 2-ClHDA and 2-ClODA adducts to GSH do not directly mirror 2-ClHDA and 2-ClODA levels. Instead, there appears to be differential metabolism of 2-ClHDA and 2-ClODA to their GSH adducts (FIG. 8B). Both HDA-GSH (2-ClHDA adduct with GSH) and ODA-GSH (2-ClODA adduct with GSH) are elevated by 15 min, but HDA-GSH levels are significantly elevated over ODA-GSH levels. At 30 min, HDA-GSH and ODA-GSH levels are not significantly different. However, at 60 min ODA-GSH levels are significantly greater than HDA-GSH. The discrepancy between 2-ClHDA and 2-ClODA adduction to GSH may be result of cellular control over the synthesis of GSH adducts or the metabolism of GSH adducts once they are made.

Importantly, α-ClFAlD production can be abolished in primary human neutrophils with the addition of aminotriazole. Both 2-ClHDA and 2-ClODA levels were greatly reduced in 200 nM PMA treated neutrophils at 30 min (FIG. 8A). Likewise, HDA-GSH and ODA-GSH levels were significantly reduced in 200 nM PMA treated neutrophils at 30 min as well (FIG. 8B). Inhibition of α-ClFAlD and their proposed adducts of GSH (HDA-GSH and ODA-GSH) by aminotriazole demonstrate that the α-ClFAlD are likely the primary, if not only, source of HDA-GSH and ODA-GSH in human neutrophils.

FALD-GSH is a biomarker of bromine and chlorine gas exposures. FALD-GSH adducts are made as a result of α-halofatty aldehydes reacting with glutathione (GSH). The α-halofatty aldehydes that the inventors have previously identified are α-chlorofatty aldehydes and α-bromofatty aldehydes, which are produced as a result of either hypochlorous acid and hypobromous acids, respectively targeting plasmalogens. They have also shown that the halogen gases, chlorine and bromine also react similarly with plasmalogens yielding these α-halofatty aldehydes. Accordingly, they are interested in the production of α-halofatty aldehydes and related compounds as biomarkers of halogen gas exposure.

Plasma samples from mice exposed to bromine and chlorine were analyzed by LC/MS with SRM detection of FALD-GSH (including HDA-GSH and ODA-GSH) as described in the manuscript (Appendix A). Mice were exposed to 600 ppm bromine for 30 min and then returned to room air. At indicated times plasma and lung was collected from these mice and the FALD-GSH was quantified. FIG. 10B shows robust increases in FALD-GSH in the plasma of mice following bromine gas exposure while FIG. 10A shows the FALD-GSH elvations in the lung. No adduct is observed in the plasma of mice exposed to air only (the first bar). Seventy-two hr following exposure, the amount of adduct in the plasma is still detectable but has decreased indicating that the FALD-GSH is metabolically cleared over time. By Ninety-six hours very little FALD-GSH is detectable.

Additional studies examined these adducts in the plasma of mice exposed to chlorine gas. For these studies mice were exposed to 400 ppm chlorine for 30 min and then returned to room air. At indicated times plasma was collected from these mice and the FALD-GSH was quantified. Data from this experiment is shown in FIG. 11. The 0 hr data refers to the mice immediately after exposure to chlorine gas. It should be appreciated that FALD-GSH is significantly increased in the plasma following chlorine gas exposure including 24 h post exposure. In contrast to bromine exposure, the plasma levels of FALD-GSH are about 8-fold lower in chlorine exposed mice. This difference likely represents the increase reactivity of 2-Br-FALD compared to 2-Cl-FALD. It is well known that bromine is a better leaving group compared to chlorine during nucleophilic attack as occurs with glutathione targeting the α-carbon of these two fatty aldehydes. From a human health and disease perspective, these findings are significant since eosinophils contain eosinophil peroxidase that selectively produces hypobromous acid, and thus eosinophils make α-bromofatty aldehydes and FALD-GSH from α-bromofatty aldehydes when activated (data not shown). Collectively, these data shows FALD-GSH is an excellent biomarker for halogen gas exposure, and the increased signal with bromine suggests FALD-GSH will be an excellent biomarker of eosinophil based diseases.

Figure 12:
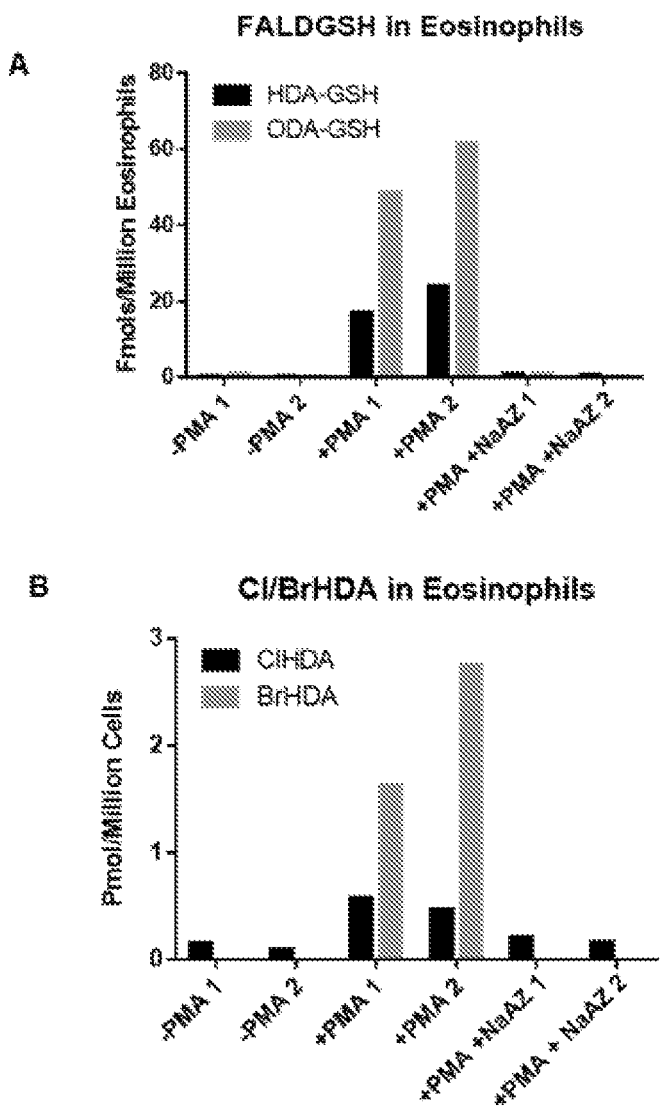
FIG. 12A-B. FALD-GSH accumulation in PMA-stimulated eosinophils.

Eosinophils isolated from allergen-hypersensitive individuals were suspended in Hanks' balanced salt solution containing 100 micromolar NaBr at a concentration of $10^6$ cells/ml for 1 h under the indicated conditions (with and without 200 nM PMA and with and without the eosinophil peroxidase activity inhibitor, sodium azide (NaAZ). Duplicates of each condition (1 and 2 in FIG. 12) were independently incubated. Following incubations, cell suspensions were snap frozen, and subsequently FALD-GSH was quantified using $[d_4]$-HDA-GSH as internal standard and the LC/MS/MS method described herein. The data show the eosinophil peroxidase-dependent production of HDA-GSH and ODA-GSH in PMA-stimulated eosinophils.

In FIG. 12B, it should be appreciated that levels of α-halofatty aldehydes are 20-fold lower in eosinophils compared to neutrophils (FIG. 8A) yet similar levels of FALD-GSH are produced (FIG. 12A. This is because Eosinophils produce primarily 2-Br-FALD, which reacts much faster with glutathione than 2-Cl-FALD produced by neutrophils.

Figure 13:
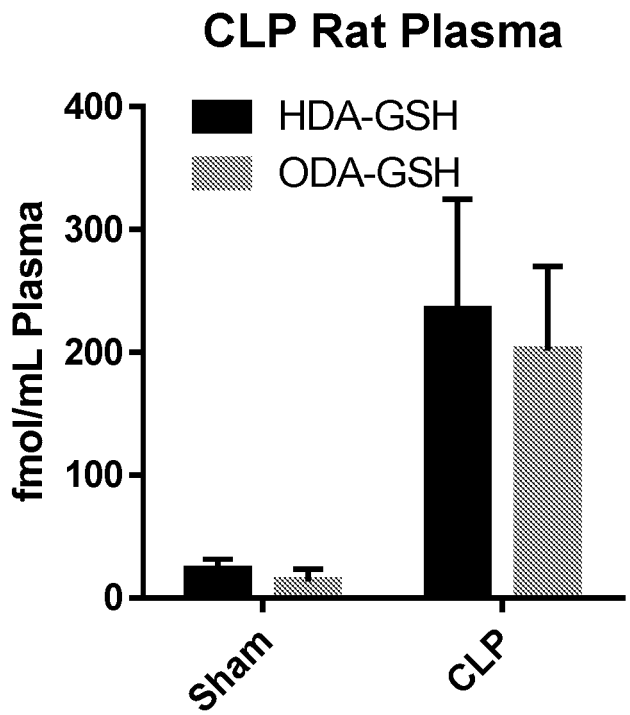
FIG. 13. CLP Septic Rat Plasma.
Figure 14:
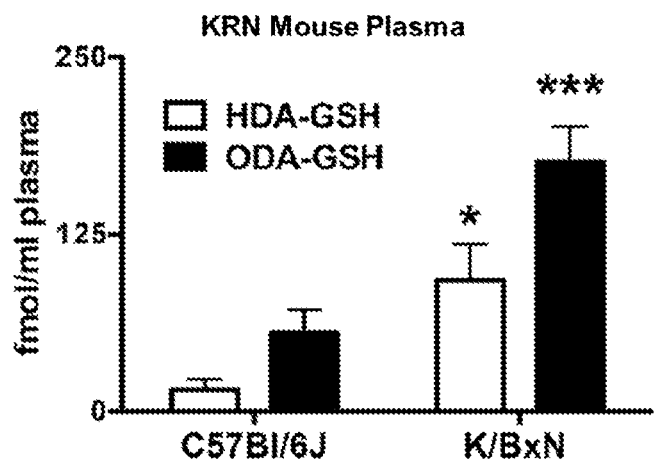
FIG. 14. Plasma levels of FALD-GSH and α-ClFA are elevated in K/BxN murine model of arthritis. 2-ClHA and 2-ClOA as well as HDA-GSH and ODA-GSH were quantitated from mouse plasma by LC-MS/MS. n=3 for each treatment.  and * indicate $p<0.01$ and $0.001$, respectively, for comparisons between C57Bl/6J and K/BxN mice of each indicated analyte.

FALD-GSH is a biomarker for sepsis and arthritis. Both sepsis and arthritis induce leukocyte activation and the production of FALD-GSH is expected. In the plasma of a rat cecal ligation puncture (CLP) model of sepsis (FIG. 13), FALD-GSH was found to be elevated relative to sham control rats. Additionally, FALD-GSH is increased in ten-week old K/BxN mice with inflammation-induced arthritis compared to C57Bl/6J control mice (FIG. 14). Both models display elevations of FALD-GSH in the plasma due to leukocyte activation through inflammatory pathologies.

Conclusion. FALD-GSH is a different biomarker for reactions in the body that are mediated by hypohalous acids or halogens. In comparison to chlorotyrosine and bromotyrosine, FALD-GSH differs by its production through a different metabolic pathway starting with targeting a different biomolecule, which then yields the biomarker (e.g., tyrosine versus plasmalogen for the FALD-GSH). In comparison to 2-chlorofatty acids, FALD-GSH differs in that for this biomarker 2-halofatty aldehyde reacts with glutathione to yield the adducts described in this disclosure rather than being oxidized to yield the 2-halofatty acid (e.g., 2-chlorofatty acid). These FALD-GSH adducts are stable over a longer period of time compared to halotyrosine. One additional difference with FALD-GSH compared to 2-chlorofatty acid is that FALD-GSH is a peptidoaldehyde that can be used as an antigen to develop antibodies for detection.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

U.S. Pat. No. 5,838,002
U.S. Pat. No. 5,788,166
U.S. Pat. No. 5,757,994
U.S. Pat. No. 3,817,837
U.S. Pat. No. 3,850,752
U.S. Pat. No. 3,939,350
U.S. Pat. No. 3,996,345
U.S. Pat. No. 4,277,437
U.S. Pat. No. 4,275,149
U.S. Pat. No. 4,366,241
U.S. Pat. No. 5,986,258
RE 35,413
Abbondanzo et al., *Ann Diagn Pathol.*, 3(5):318-327, 1999.
Albert et al., (2003) *Journal of Biological Chemistry* 278, 8942-8950, 2003.
Allred et al., *Arch Surg.*, 125(1):107-13, 1990.
Bahr et al., *J Mass Spectrom.*, 32:1111-1116, 1997.
Bentzley et al., *Anal Chem.*, 68(13):2141-2146, 1996.
Brown et al., *Immunol. Ser.*, 53:69-82, 1990.
Bucknall et al., *J. Am. Soc. Mass Spectrom.*, 13(9):1015-1027, 2002.
Caprioli et al., *Anal. Chem.*, 69:4751, 1997.
Chaurand et al., *J. Am. Soc. Mass. Spect.* 71(23):5263-5270, 1999.
Cooper and Hanigan, "Enzymes involved in processing glutathione conjugates." In *Comprehensive Toxicology* (McQueen, C. A. ed.), 2nd Ed., Elsevier. pp 323-365, 2010.
Chen et al., *Nat. Biotechnol.*, 19:537-542, 2001.
De Jager et al., *Semin Nucl Med* 23(2):165-179, 1993.
Desiderio et al., *Methods Mol. Biol.*, 61:57-65, 1996.
Desiderio et al., *J. Mass Spectrom.*, 35(6):725-733, 2000.
Doolittle and Ben-Zeev, *Methods Mol. Biol.*, 109:215-237, 1999.
Duncan et al., *Rapid Commun. Mass Spectrom.*, 7(12); 1090-1094, 1993.
Faulstich et al., *Anal. Chem.*, 69(21):4349-4353, 1997.
Gobom et al., *Anal. Chem.*, 72(14):3320-3326, 2000.
Gulbis and Galand, *Hum Pathol.* 24(12):1271-1285, 1993.
Horak et al., *Rapid Commun. Mass Spectrom.*, 15(4):241-248, 2001.
Jespersen et al., *Anal Chem.*, 71(3):660-666, 1999.
Jiang et al., *J. Agric. Food Chem.*, 48:3305, 2000.
Kanazawa et al., *Biol. Pharm. Bull.*, 22(4):339-346, 1999.
Kazmaier et al., *Anesthesiology*, 89(4):831-817, 1998.
Li et al., *Trends Biotechnol.*, 18:151, 2000.
Lovelace et al., *J Chromatogr* 562(1-2):573-584, 1991.
Lynn et al., *J Mol. Evol.*, 48(5):605-614, 1999.
Marie et al., *Anal. Chem.*, 66:1408, 2000.

Mirgorodskaya et al., *Rapid Commun. Mass Spectrom.*, 14(14):1226-1232, 2000.
Miketova et al., *Mol. Biotechnol.*, 8(3):249-253, 1997.
Muddiman et al., *Fres. J Anal. Chem.*, 354:103, 1996.
Nakamura et al., In: Handbook of Experimental Immunology (4.sup.th Ed.), Weir et al., (eds). 1:27, Blackwell Scientific Publ., Oxford, 1987.
Nelson et al., *Anal. Chem.*, 66:1408, 1994.
Nguyen et al., *J. Chromatogr. A.*, 705(1):21-45, 1995.
Roepstorff et al., *EXS* 88:81-97, 2000.
Stoeckli et al., *Nat. Med.*, 7(4):493-496, 2001.
Takach et al., *J. Protein Chem.*, 16:363, 1997.
Thukkani et al., *J Biol Chem* 278, 36365-36372, 2003.
Thukkani et al., *Am J. Physiol-Heart Circ Physiol* 288, H2955-2964, 2005.
Villanueva et al., *Enzyme Microb. Technol.*, 29:99, 1999.
Wang et al., *J Agric. Food Chem.*, 47:1549, 1999.
Wang et al., *Anal. Chem.*, 72(21):5285-5289, 2000.
Wittmann et al., *Biotechnol. Bioeng.*, 72:642, 2001.
Wu et al., *Biochim. Biophys. Acta*, 1466:315-327, 2000.
Wu et al., *Anal. Chem.*, 70:456 A, 1998.
Wu et al., *Biochem. Biophys. Res. Commun.*, 233(1):221-226, 1997.
Yang et al., *J. Agric. Food. Chem.*, 48:3990, 2000.
Zhong et al., *Clin. Chem. Acta*, 313:147, 2001.
Zweigenbaum et al., *J. Pharm. Biomed. Anal.*, 23(4):723-733, 2000.
Zweigenbaum et al., *Anal. Chem.*, 71(13):2294-300, 1999.

What is claimed:

1. A method of diagnosing a subject as having or being at risk of developing a leukocyte-mediated disease (LMD) comprising:
   (a) detecting the level of glutathione adducts of 2-halofatty aldehydes (FALD-GSH) in a sample using mass spectrometry and a deuterated non-natural analog of said FALD-GSH as standard;
   (b) comparing the level of FALD-GSH determined in step (a) with a known value reflective of levels of FALD-GSH in health and/or disease subjects; and
   (c) diagnosing said subject as having or being at risk of developing LMD if the level of FALD-GSH in said sample is (i) higher than said known value for a healthy subject and/or (ii) similar to said known value for a disease subject.

2. The method of claim 1, wherein said sample is blood, plasma, serum, sputum, urine, nasal swab, or ear wax.

3. The method of claim 1, wherein said subject is suspected of having LMD.

4. The method of claim 1, wherein said subject exhibits one or more symptoms of LMD.

5. The method of claim 1, wherein said subject does not exhibit a symptom of LMD.

6. The method of claim 1, wherein detecting comprises (i) mass spectrometry and/or high performance liquid chromatograph (HPLC), or (ii) binding of an antibody to FALD-GSH.

7. The method of claim 1, further comprising performing steps (a) and (b) at a second time point to determine progression of LMD or to determine the efficacy of an intervening treatment.

8. The method of claim 1, further comprising treating said subject if LMD is diagnosed.

9. The method of claim 1, wherein LMD is selected from the group consisting of asthma, sepsis, atherosclerosis, myocardial infarction and eosinophilic esophagitis.

10. The method of claim 1, wherein said standard or control comprises detected labeled FALD-GSH.

11. The method of claim 1, wherein the glutathione adduct is an adduct of 2-bromofatty aldehyde or 2-chlorofatty aldehyde.

12. The method of claim 1, wherein the glutathione adduct is hexadecanal glutathione or octadecanal glutathione.

13. The method of claim 1, further comprising obtaining said sample from said subject.

14. The method of claim 6, wherein an antibody binding to FALD-GSH is employed in immunoprecipitation, Western blot or ELISA.

15. The method of claim 6, wherein mass spectrometry and HPLC are used.

* * * * *